(12) United States Patent  (10) Patent No.: US 8,277,374 B2
Tsumaru et al.  (45) Date of Patent: Oct. 2, 2012

(54) MEDICAL INSTRUMENT, ENDOSCOPE AND ENDOSCOPE DEVICE

(75) Inventors: Masayo Tsumaru, Sagamihara (JP); Ryuichi Toyama, Hachioji (JP); Makoto Abe, Hino (JP); Toshihiro Hadano, Hachioji (JP); Ryosuke Ishizaki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1006 days.

(21) Appl. No.: 12/260,604

(22) Filed: Oct. 29, 2008

(65) Prior Publication Data

US 2009/0118582 A1  May 7, 2009

(30) Foreign Application Priority Data

Nov. 6, 2007  (JP) .................................. 2007-288924

(51) Int. Cl.
*A61B 1/04*  (2006.01)

(52) U.S. Cl. ......... 600/115; 600/114; 600/116; 600/156

(58) Field of Classification Search .......... 600/114–116, 600/156
See application file for complete search history.

(56) References Cited

U.S. PATENT DOCUMENTS

| 4,934,786 | A | * | 6/1990 | Krauter | 385/118 |
| 5,129,910 | A | * | 7/1992 | Phan et al. | 606/127 |
| 5,906,591 | A | * | 5/1999 | Dario et al. | 604/95.03 |
| 5,989,230 | A | * | 11/1999 | Frassica | 604/264 |
| 7,022,068 | B2 | | 4/2006 | Kim et al. | |
| 7,048,717 | B1 | * | 5/2006 | Frassica | 604/165.04 |
| 7,066,880 | B2 | * | 6/2006 | Wendlandt | 600/114 |
| 7,955,253 | B2 | * | 6/2011 | Ewers et al. | 600/114 |
| 2003/0083546 | A1 | * | 5/2003 | Butler et al. | 600/114 |

FOREIGN PATENT DOCUMENTS

JP  2006-034627  2/2006

* cited by examiner

*Primary Examiner* — Matthew J Kasztejna
(74) *Attorney, Agent, or Firm* — Scully, Scott, Murphy & Presser, P.C.

(57) ABSTRACT

A medical instrument of the present invention comprises a spiral shaped portion provided at an insertion portion main body, for generating a force at the insertion portion main body to advance/retreat in a subject by a contact with a body wall of the subject, a balloon provided so as to expand radially in a radial direction of the insertion portion main body and capable of contact with the body wall, a suction opening portion provided between the spiral shaped portion and the balloon in the insertion portion main body, and a suction pipeline communicating with the suction opening portion, inserted into the insertion portion main body and connected to a suction pressure controller on a rear end side of the insertion portion main body in the insertion direction.

15 Claims, 16 Drawing Sheets

MEDICAL INSTRUMENT, ENDOSCOPE AND ENDOSCOPE DEVICE

CROSS REFERENCE TO RELATED APPLICATION

This application claims benefit of Japanese Application No. 2007-288924 filed in Japan on Nov. 6, 2007, the contents of which are incorporated by this reference.

BACKGROUND OF THE INVENTION

1. Field of the Invention

The present invention relates to a medical instrument which is provided with an insertion portion automatically inserted into a subject, an endoscope, and an endoscope device.

2. Description of the Related Art

In recent years, medical instruments such as endoscopes have been widely used in the medical field and industrial field. The endoscope used in the medical field is used for observing organs in a body cavity by inserting an elongated insertion portion into a body cavity as a subject or conducting various treatments using a treatment instrument inserted into an insertion channel of the treatment instrument provided at the endoscope as necessary.

When the insertion portion of a medical endoscope is inserted into a tract in a body cavity such as a colon through an anus, for example, an operator advances the insertion portion in the colon by applying a twisting operation and a feeding operation to a portion located outside the body cavity of the insertion portion and at a bent portion in the colon, the operator advances the insertion portion by bending a bending portion through operation of a bending operating member provided at an operation portion. There is generally known an art to insert the insertion portion to a portion being tested in the colon by the above twisting operation and the feeding operation of the insertion portion and the bending operation of the bending portion.

Here, the above-mentioned insertion operation to the insertion portion of the endoscope, particularly in a colon having a complex and intricate shape, requires skill till the operation can be performed to the depth of the colon smoothly and in a short time.

Therefore, an operator with less experience might take time in operation since the operator loses an insertion direction of the insertion portion, for example, or changes a running state of the colon during performing the insertion operation.

Thus, an endoscope that enables even an operator with less experience to easily insert the insertion portion of the endoscope into a tract in a body cavity and to advance the insertion portion to the portion being tested is in demand.

In view of the above circumstances, Japanese Patent Application Laid-Open Publication No. 2006-034627 discloses a self-propelled endoscope in which a spiral structural body is provided with a spiral shaped portion at a distal end side in an insertion direction of an insertion portion and a thrust is generated at the insertion portion by contact of the spiral structural body with an inner wall of a tract in a body cavity, accompanied by rotary motion, so that the insertion portion is automatically advanced in the tract in the body cavity.

A self-propelled endoscope is also known in which a spiral shaped portion for generating a thrust at the insertion portion by contact with the inner wall of the tract in the body cavity, accompanied by rotary motion, is provided over the entire length of the insertion portion.

SUMMARY OF THE INVENTION

A medical instrument of the present invention in brief is a medical instrument provided with an insertion portion to be automatically inserted into a subject, including a thrust member provided at the insertion portion, for generating a force to advance/retreat in the subject at the insertion portion by contact with a body wall of the subject being tested, a contact member provided so as to radially expand in the radial direction of the insertion portion in the insertion portion and capable of contact with the body wall, a suction opening portion provided between the thrust member and the contact member in the insertion portion, and a suction pipeline inserted into the insertion portion and communicating with the suction opening portion connected to a suction device at a rear end side in an insertion direction of the insertion portion.

The above and other objects, features and advantages of the invention will become more clearly understood from the following description referring to the accompanying drawings.

DETAILED DESCRIPTION OF THE PREFERRED EMBODIMENTS

Embodiments of the present invention will be described below referring to the attached drawings. In the embodiments shown below, a medical self-propelled endoscope will be explained as an example of the medical instrument. Also, a rotary self-propelled endoscope will be explained as an example of the self-propelled endoscope.

First Embodiment

Figure 1:
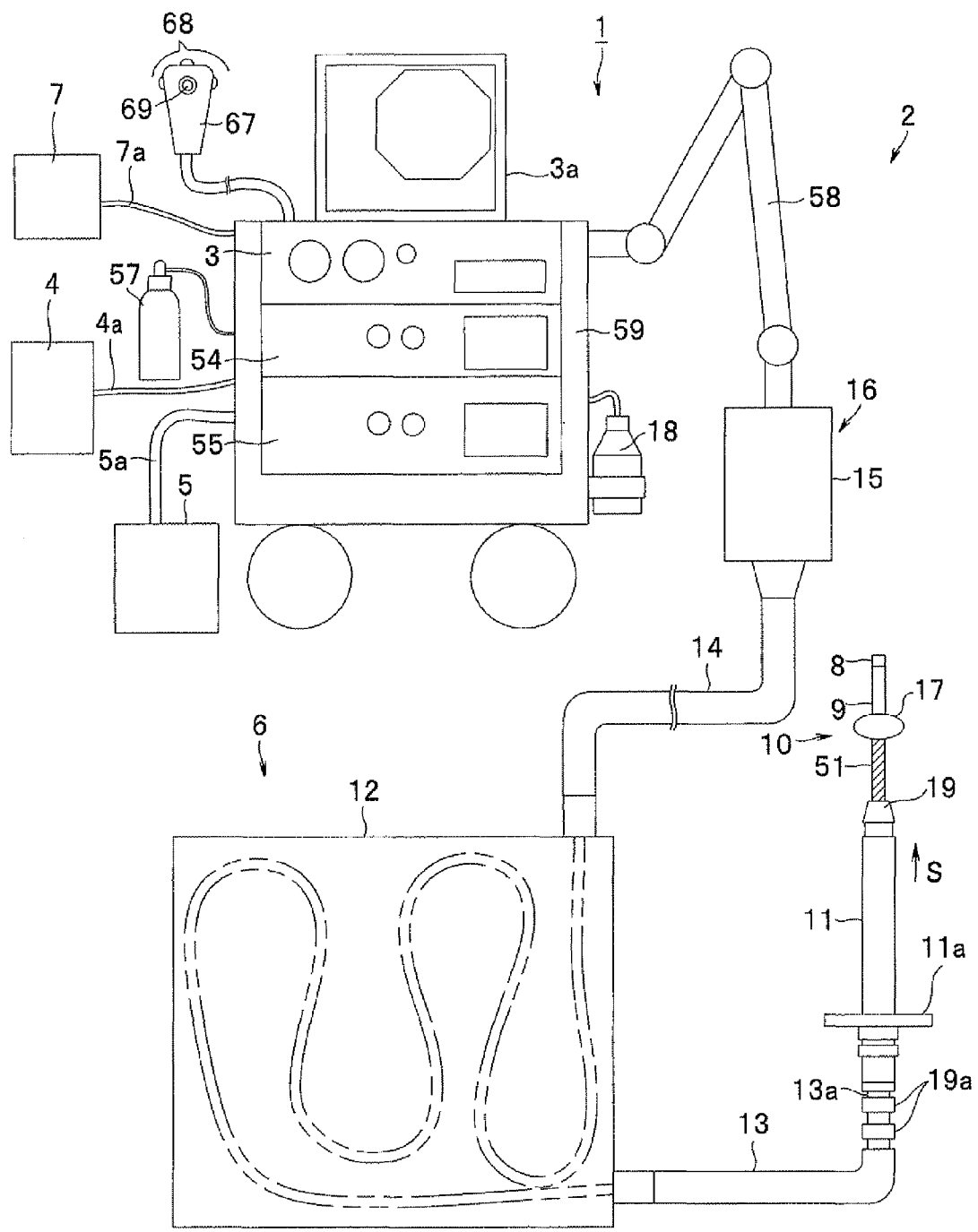
FIG. 1 is a diagram illustrating an outline of configuration of an endoscope device provided with a rotary self-propelled endoscope showing a first embodiment.
Figure 2:
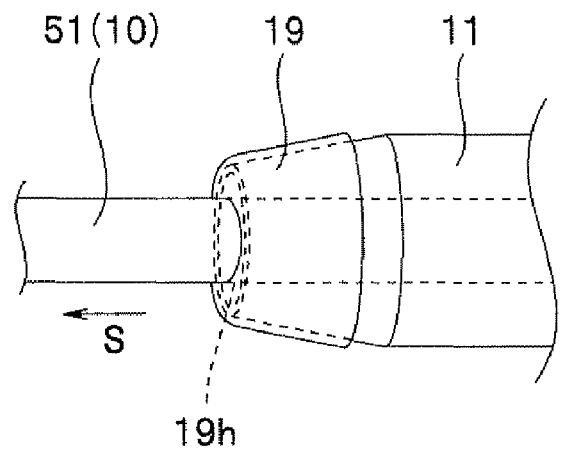
FIG. 2 is a partial perspective view of an insertion portion in the vicinity of an air-tightness keeping member of the rotary self-propelled endoscope in FIG. 1.
Figure 3:
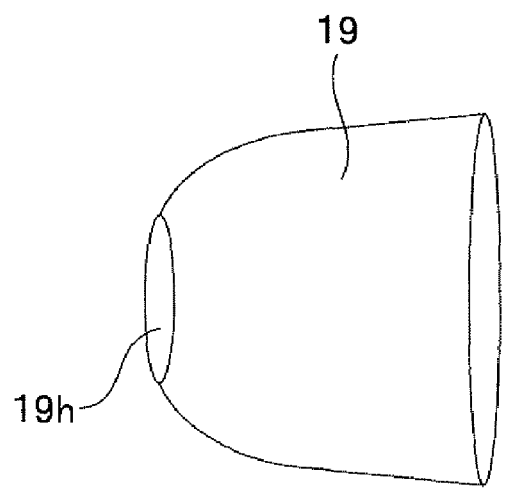
FIG. 3 is an enlarged perspective view of the air-tightness keeping member in FIG. 2.

FIG. 1 is a diagram illustrating an outline of configuration of an endoscope device provided with a rotary self-propelled endoscope showing a first embodiment, FIG. 2 is a partial perspective view of an insertion portion in the vicinity of an air-tightness keeping member of the rotary self-propelled endoscope in FIG. 1, and FIG. 3 is an enlarged perspective view of the air-tightness keeping member in FIG. 2.

Figure 4:
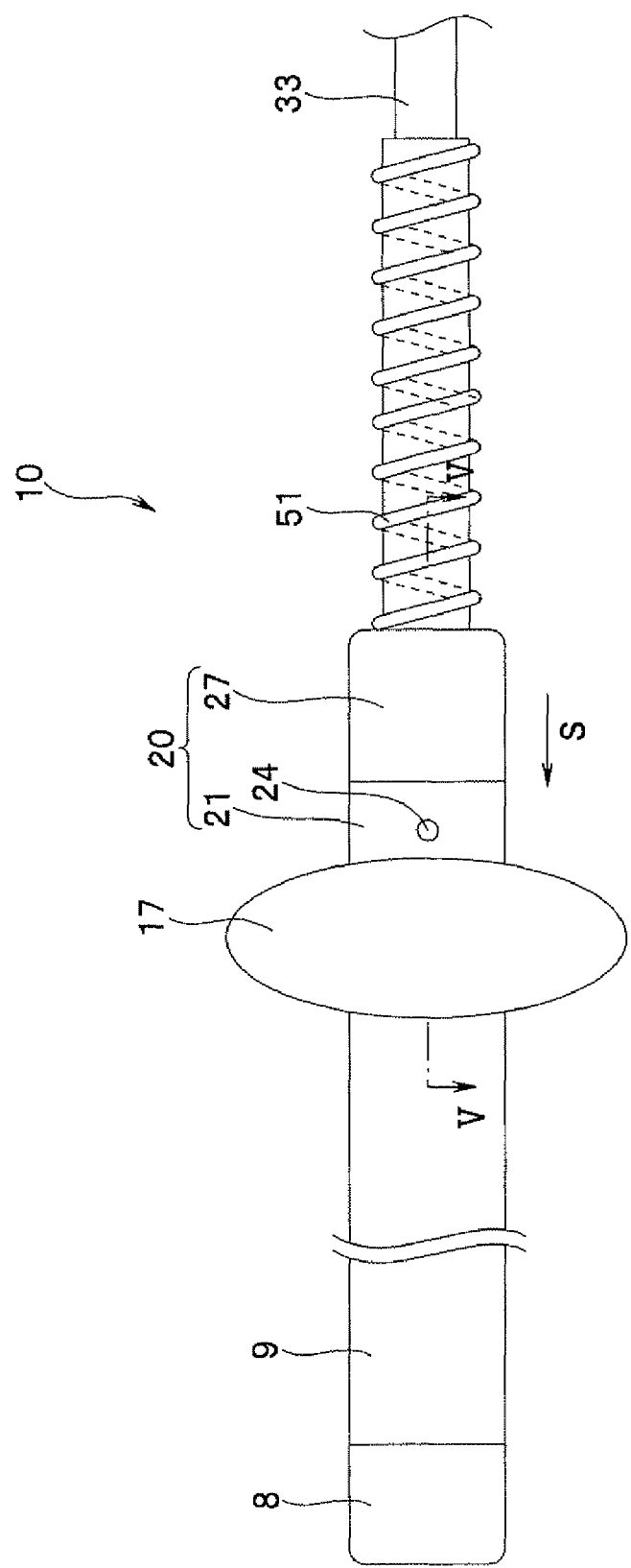
FIG. 4 is a partially enlarged plan view of a distal end side in an insertion direction of an insertion portion main body in the rotary self-propelled endoscope in FIG. 1.
Figure 5:
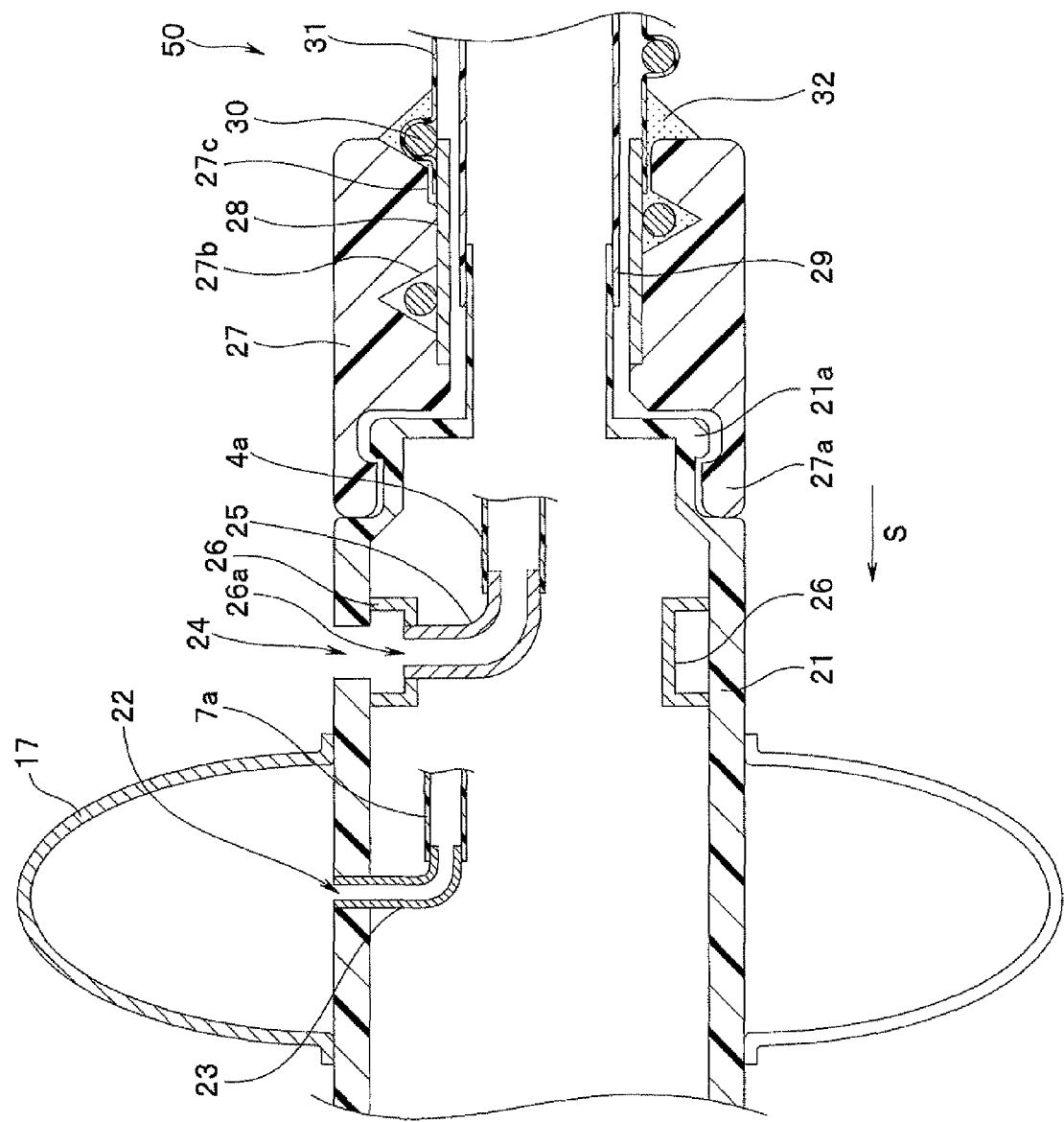
FIG. 5 is a partially enlarged sectional view of the insertion portion main body along V-V line in FIG. 4.
Figure 6:
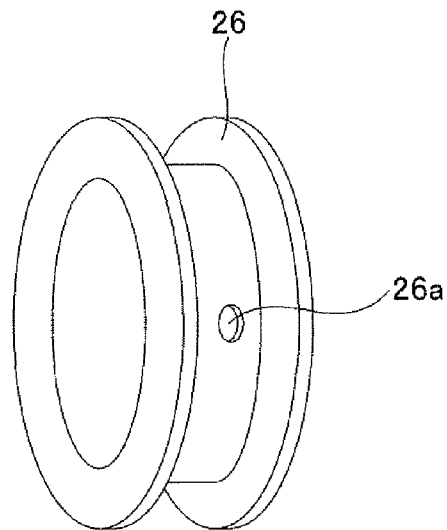
FIG. 6 is an enlarged perspective view of a suction partition member in FIG. 5.
Figure 7:
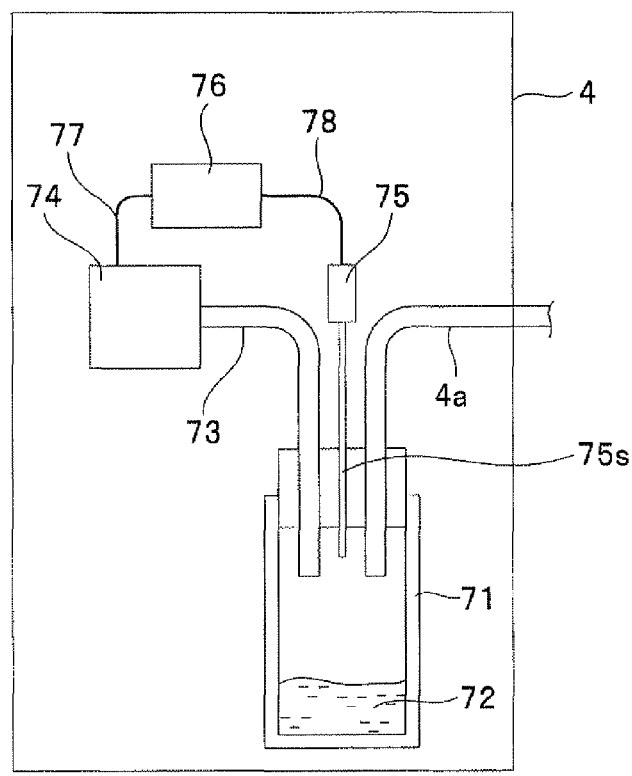
FIG. 7 is a diagram illustrating configuration of the inside of a suction-pressure controller in FIG. 1.

Also, FIG. 4 is a partially enlarged plan view of a distal end side in an insertion direction of an insertion portion main body in the rotary self-propelled endoscope in FIG. 1, FIG. 5 is a partially enlarged sectional view of the insertion portion main body along V-V line in FIG. 4, FIG. 6 is an enlarged perspective view of a suction partition member in FIG. 5, and FIG. 7 is a diagram illustrating configuration of the inside of a suction-pressure controller in FIG. 1.

As shown in FIG. 1, an endoscope device 1 has an essential part configured by a rotary self-propelled endoscope (hereinafter simply referred to as an endoscope) 2, a first controller 3, a monitor 3a, a suction pressure controller 4, which is a suction device, a suction device 5, an in-balloon controller 7, a second controller 54, and a third controller 55.

The first controller 3, the monitor 3a, the second controller 54, and the third controller 55 are mounted on a trolley 59 with a caster.

The endoscope 2 has an essential part configured by an insertion portion 6 and a motor box 16. The insertion portion 6 has an essential part configured by an insertion portion main body 10, an insertion assisting tool 11, a distal-end side guide tube 13, an insertion portion container case 12, and a cover-side guide tube 14. The insertion portion 6 has configuration either of a disposable type to be disposed of after every use or a type capable of reuse by sufficient sterilization after use.

The insertion portion main body 10 has an essential part configured in order from the distal end side in an insertion direction S by a distal end portion 8, a bending portion 9, a spiral tube connection base 21 (See FIG. 4), a distal-end side base 27 (See FIG. 4), a spiral shaped portion 51, and a flexible shaft 33 (See FIG. 4). Detailed configuration of the insertion portion main body 10 will be described later using FIGS. 4 and 5.

The insertion assisting tool 11, the distal-end side guide tube 13, the insertion portion container case 12, the cover-side guide tube 14, and a connector cover 15 covers the insertion portion main body 10 in order from the distal end side in the insertion direction S. Also, the distal-end side guide tube 13 and the cover-side guide tube 14 are constituted by a corrugated state tube.

The insertion assisting tool 11 is inserted from an anus into a subject being tested such as a colon, for example, at an examination, in order to prevent rotation of the spiral shaped portion 51 and the flexible shaft 33 from being disturbed by tightening of the anus.

The insertion assisting tool 11 is formed to become gradually thin on the distal end side in the insertion direction S so as to be easily inserted into the intestine from the anus. Also, on the rear end side of the insertion assisting tool 11 in the insertion direction S, a contact portion 11a having a flange shape is provided.

The insertion assisting tool 11 is formed of a resin such as polyethylene. Moreover, as shown in FIG. 2, the distal end of the insertion assisting tool 11 in the insertion direction S is covered by an air-tightness keeping member 19 blocking a gap formed between the insertion assisting tool 11 and the insertion portion main body 10.

The air-tightness keeping member 19 is, as shown in FIG. 3, formed in the substantially cup shape by a resin with rich stretching properties such as biocompatible latex rubber, synthetic rubber, thermally workable elastomer and the like. At the center in the radial direction of the air-tightness keeping member 19, a hole 19h is formed and into the hole 19h, the spiral shaped portion 51 or the flexible shaft 33 is inserted. The air-tightness keeping member 19 prevents, as shown in FIG. 2, leakage of a gas from the gap at the hole 19h between the distal end side of the insertion assisting tool 11 in the insertion direction S and the insertion portion main body 10.

At the distal end side of the distal-end side guide tube 13 in the insertion direction S, a small diameter portion 13a is formed, and at the small diameter portion 13a, a spare air-tightness keeping member 19a is provided. That is, a spare member of the air-tightness keeping member 19 is provided.

The spare air-tightness keeping member 19a is provided at the small diameter portion 13a so that when it is confirmed that the air-tightness keeping member 19 is damaged and a gas leaks from the gap at the hole 19h between the distal end side of the insertion assisting tool 11 and the insertion portion main body 10, the air-tightness keeping member 19 can be replaced, and 2 or 3 spares are inserted through the small diameter portion 13a, for example.

The insertion portion container case 12 is a case for housing the insertion portion main body 10 and has the case inside formed of Teflon (registered trademark) with good sliding performance so that the insertion portion main body 10 can smoothly move into or out of the insertion portion container case 12. The insertion portion main body 10 is, as shown in FIG. 1, contained in a looped state in the container case 12, for example.

The motor box 16 is provided with the connector cover 15, and to the connector cover 15, an end portion of the cover-side guide tube 14 is connected. Also, in the connector cover 15, a motor and the like, not shown, for rotating the spiral shaped portion 51 and the flexible shaft 33 are provided. Also, at the connector cover 15, the other end of an arm 58 having three joint parts, for example, and one end fixed to the trolley 59 is fixed.

Through the arm 58, various fluid supply tubes such as water/air feed tube, treatment instrument insertion tube and the like, which will be described later, provided at the endoscope 2 and various electric cables connected to an image pickup unit, which will be described later, provided in the distal end portion 8 and a motor in the motor box 16, respectively, are inserted. The above-mentioned various cables and tubes may be along the outer surface of the arm 58. The various fluid supply tubes and various electric cables are connected to corresponding controllers 3, 4, 5, 7, 54, 55, respectively, on the rear face side.

To a first controller 3, a remote control unit (hereinafter abbreviated as remote controller) 67 for operating various endoscope functions in a centralized manner, a suction pressure controller 4, an in-balloon controller 7, the second controller 54, the third controller 55, and the monitor 3a are electrically connected by communication cables, not shown, on the rear face side.

The first controller 3 controls image pickup unit provided at the endoscope 2, illumination unit, and driving of the motor in the connector cover 15. In more detail, the first controller 3 carries out image processing of an endoscopic image picked-up by the endoscope 2, power supply to an LED, not shown, in the illumination unit, power supply to the motor in the connector cover 15 and the like based on an input operation from an operator through the remote controller 67.

On the front face of the first controller 3, various operation switches and the like, not shown, that can be operated by the remote controller 67 are disposed. Specifically, in addition to a power switch for the first controller 3, various operation members such as a rotation speed operation dial for varying a rotation speed of the spiral shaped portion 51 and the flexible shaft 33 of the endoscope 2 and the like are disposed.

The first controller 3 is electrically connected to the monitor 3a. The monitor 3a displays an endoscopic image picked-up by the endoscope 2.

The suction pressure controller 4 sucks air and liquid in an intestine through a suction opening portion 24 (See FIG. 5), which will be described later, and is connected to the circular suction opening portion 24 through a suction tube 4a and the like. Also, the suction pressure controller 4 controls a suction pressure when the air and liquid in the intestine is sucked through the suction opening portion 24. Detailed configuration of the suction pressure controller 4 will be described later using FIG. 7.

In the in-balloon controller 7, a compressor for supplying a fluid, an air supply/discharge valve, a pressure sensor, a pressure controller and the like are provided. The in-balloon controller 7 inflates/deflates a balloon 17 in a radial direction of the insertion portion main body 10 by supplying a fluid into the balloon 17, which will be described later or sucking a fluid in the balloon 17 via an in-balloon fluid supply tube 7a. The fluid supplied into the balloon 17 is not limited to air but may be distilled water, saline water, lubricant and the like.

The second controller 54 supplies air into an air/water supply pipeline, not shown, controls supply of air into the intestine from an opening, not shown, of the air/water supply pipeline at the distal end portion 8 and also controls bending of the bending portion 9 by supplying air to a multi-lumen tube, which will be described later.

To the second controller 54, a carbon dioxide ($CO_2$) tank 57 is connected, and in the second controller 54, a compressor for supplying air, an air supply/discharge valve (either is not shown) and the like are provided.

The third controller 55 performs water supply control through an air/water supply tube, which will be described later, in the endoscope 2 and control of suction through the treatment instrument insertion tube, which will be described later, by operation input from the remote controller 67.

In the third controller 55, a pump, a valve and the like, not shown, are provided. Moreover, to the third controller 55, a water supply tank 18 is connected. In the water supply tank 18, distilled water, saline water and the like are reserved.

To the third controller 55, a suction device 5 is connected through a tube 5a. The third controller 55 controls suctioning of a body fluid and the like in the intestine into the suction device 5 by operating the pump, valve and the like through the treatment instrument insertion pipeline of the endoscope 2 when the operation input is made from the remote controller 67.

To the third controller 55, not only the suction device 5 but a suctioning system equipped in a hospital, facility and the like, for example, may be connected.

To the first controller 3, the remote controller 67 capable of operation of various functions in the endoscope 2 in a centralized manner is connected. The remote controller 67 can give operation instruction in a centralized manner to the suction pressure controller 4, the in-balloon controller 7, and three controllers 3, 54, 55, and the bending operation, rotation/stop operation of the spiral shaped portion 51 and the flexible shaft 33, air/water supply operation, suction operation, balloon inflation/deflation operation and the like are carried out by the remote controller 67. Also, the remote controller 67 has various operation switches 68 and an operation lever 69 for bending operation of the bending portion 9.

The operation switches 68 carry out instruction input such as rotation/stop operation of the spiral shaped portion 51 and the flexible shaft 33, air/water supply operation, suctioning operation, balloon inflation/deflation operation and the like. The above operations may be made from a foot switch, not shown, connected to the first controller 3. The operation lever 69 is constituted by a joy-stick type, for example, for making a bending operation of the bending portion 9.

Next, configuration of a distal end side of the insertion portion main body 10 of the insertion portion 6 of the endoscope 2 in the insertion direction S will be described using FIGS. 4 to 6.

The insertion portion main body 10 has, as shown in FIG. 4, an essential part configured by the distal end portion 8, the bending portion 9, the spiral tube connection base 21, the distal-end side base 27, the spiral shaped portion 51, and the flexible shaft 33 in order from the distal end side of the insertion direction S.

In the distal end portion 8, an image pickup unit provided with an objective lens group, image pickup devices, which are photoelectric conversion devices such as a CCD (Charge Coupled Device), a CMOS (Complementary Metal Oxide Semiconductor) and the like arranged on an optical axis of the objective lens group, and a flexible print board (none of them is shown) is disposed. Also, in the distal end portion 8, a plurality of LEDs as an illumination portion are disposed so as to surround the above-mentioned objective lens group.

In the distal end portion 8, in a gap formed between the above-mentioned image pickup unit and the LED, the treatment instrument insertion tube in which the treatment instrument insertion pipeline also functioning as a suction pipeline is formed, the air/water supply tube in which the air/water supply pipeline is formed and the like are inserted, and on a distal end face of the distal end portion 8, a distal end side of the treatment instrument insertion pipeline and air/water supply pipeline in the insertion direction S is opened.

In the bending portion 9, a known multi-lumen tube in which a lumen, which is a plurality of hole portions, is formed along the insertion direction S is disposed, and the bending portion 9 is configured to bend by supplying a fluid into the multi-lumen tube.

In the multi-lumen tube, an electric cable of the above-mentioned image pickup unit, an electric cable of the LED, the treatment instrument insertion tube, the air/water supply tube and the like are inserted. The bending portion 9 may be configured to bend by a known pulling operation of a wire.

As shown in FIG. 4, at a rear end portion of the bending portion 9 in the insertion direction S, the spiral tube connection base 21 constituting a connection portion 20 is provided. At the rear end portion of the spiral tube connection base 21 in the insertion direction S, an engagement portion 21a is provided as shown in FIG. 5. The engagement portion 21a is engaged with a projection portion 27a of the distal-end side base 27, which will be described later, provided at the distal end of the spiral shaped portion 51 in the insertion direction S.

As shown in FIG. 5, at the rear end portion of the engagement portion 21a in the insertion direction S, the distal end side of an inner cylindrical tube 29 in the insertion direction S is fitted and fixed. The inner cylindrical tube 29 is formed by a tube body and the like having flexibility formed by cylindrically braiding a thin wire and the like.

Inside the inner cylindrical tube 29, a signal cable, not shown, including an electric cable of the LED, not shown, and various tubes such as the suction tube 4a, in-balloon fluid supply tube 7a and the like are inserted. As a result, the inner cylindrical tube 29 protects the various cables and various tubes. The signal cable may be inserted with a coating (ground line) on a signal cable outer circumference portion removed in order to soften the insertion portion and to improve insertion performance.

As shown in FIGS. 4 and 5, the balloon 17, which is a contact member capable of being in contact with the intestinal wall so that the balloon expands radially in the radial direction of the insertion portion main body 10 is provided at the spiral tube connection base 21 by an adhesive, not shown, or thread-winding plus adhesion.

The balloon 17 is capable of inflation/deflation in the radial direction of the insertion portion main body 10. The balloon 17 is fixed to the spiral tube connection base 21 so that the balloon does not rotate around a shaft in the longitudinal direction of the insertion portion main body 10 in the insertion direction S.

Figure 8:
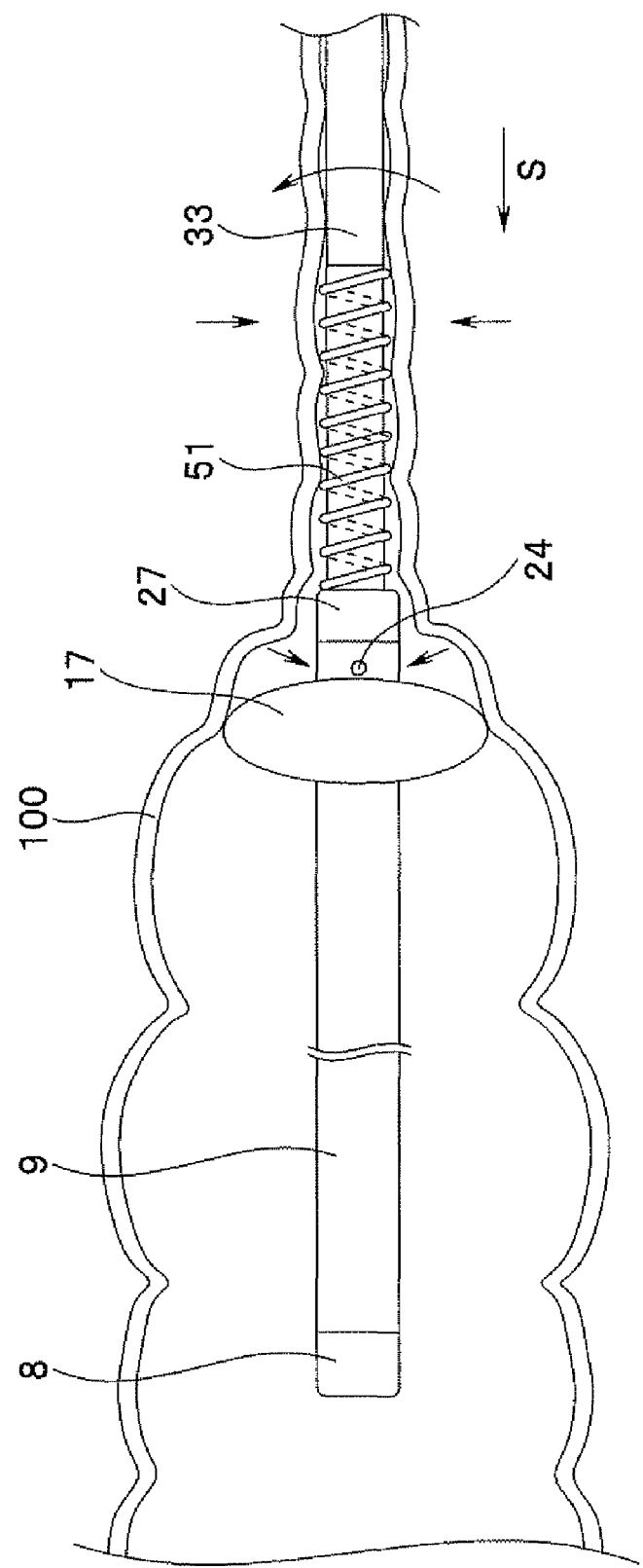
FIG. 8 is a diagram schematically illustrating the distal end side in the insertion direction of the insertion portion main body in FIG. 4 in a state inserted into an intestine.

On the outer surface of the balloon 17, hydrophilic lubrication treatment is applied in order to reduce friction with an intestinal wall 100 (See FIG. 8). In order to reduce friction with the intestinal wall 100, a small hole may be provided at the spiral tube connection base 21 at the rear end side than the balloon 17 in the insertion direction S so that the lubricant is poured through the hole.

Also, it may be so configured that a small hole is provided at the balloon 17 itself, the balloon 17 is inflated by the lubricant and when the balloon 17 is inflated, the lubricant flows out of the hole at the balloon 17. In this case, the periphery of the hole is reinforced by an adhesive or the like so that the small hole provided at the balloon 17 is not expanded.

When a fluid is supplied into the balloon 17 and the balloon 17 is inflated, the balloon 17 is brought into contact with the intestinal wall 100 and closes a part of a space in the intestine. The contact member in contact with the intestinal wall 100 is not limited to the balloon 17 but may be a soft projection which will not damage the intestinal wall 100, for example.

On the outer surface of the spiral tube connection base 21, at least one or more in-balloon fluid supply holes 22 are provided so as to communicate with inside of the balloon 17. Also, in order to communicate with the hole 22, one end side of an L-shaped pipe 23 for balloon is fitted in the in-balloon fluid supply hole 22. At the other end of the L-shaped pipe 23 for balloon, the in-balloon fluid supply tube 7a connected to the in-balloon controller 7 is externally inserted and bonded and fixed. The in-balloon fluid supply tube 7a is formed of a fluorine resin material provided with some degree of flexibility and the like.

On the outer surface of the spiral tube connection base 21, one or more suction opening portions 24 are formed in the rear of the insertion direction S than the balloon 17. The suction opening portion 24 is, as shown in FIG. 4, formed between the balloon 17 and the spiral shaped portion 51. The suction opening portion 24 is connected to the suction pressure controller 4 through an L-shaped pipe 25 for suction and the suction tube 4a and the control pressure is controlled by the suction pressure controller 4.

The one end side of the L-shaped pipe 25 for suction is fitted in a suction hole 26a so as to communicate with the suction hole 26a provided at a suction partition member 26. To the other end side of the L-shaped pipe 25 for suction, the suction tube 4a is externally inserted and bonded and fixed.

The suction tube 4a is to have the suction opening portion 24 and a suction bin 71 (See FIG. 7) communicate with each other through the suction partition member 26 and the L-shaped pipe 25 for suction and is formed of a fluorine resin material and the like provided with some degree of flexibility.

The suction partition member 26 has, as shown in FIG. 6, a shape provided with a flange at both ends in the thickness direction of the cylindrical member. By bringing the outer circumferential face of the flange into contact with the inner circumferential face of the spiral tube connection base 21, the flange is disposed on the inner circumference side than the suction opening portion 24.

On the inner circumferential face of the suction partition member 26 in the radial direction, the suction hole 26a is provided, and the L-shaped pipe 25 for suction is fitted in the suction hole 26a. By the suction partition member 26, an annular pipeline is formed in a space surrounded by the flange, the cylindrical portion, and the inner circumferential face of the spiral tube connection base 21. Thus, by disposing the suction partition member 26, even if the plurality of suction opening portions 24 are provided, suction can be carried out by the single suction tube 4a through the annular pipeline.

The distal-end side base 27 constituting the connection portion 20 is a member provided at the distal end portion of the spiral shaped portion 51 in the insertion direction S, and the projection portion 27a provided at the distal end portion of the distal-end side base 27 in the insertion direction S is engaged with the engagement portion 21a of the spiral tube connection base 21.

Also, on the inner circumferential face at the rear end side of the distal-end side base 27 in the insertion direction S, a spiral groove 27b is formed, and the spiral shaped portion 51 is screwed in the spiral groove 27b. Moreover, at the distal-end side base 27, at the rear end side than the spiral groove 27b, a resin coated groove 27c is formed.

The distal-end side base 27 is rotatable around the axis in the insertion direction S with respect to the spiral tube connection base 21 in an engaged state with the spiral tube connection base 21.

At the distal-end side base 27, in a range where the resin coated groove 27c is provided, a portion provided on the outer circumference side of a spiral body 30 in a resin coating 31 of the spiral shaped portion 51 is inserted and bonded and fixed. In this case, the resin coating 31 prevents flowing of an adhesive 32 filled in a gap among the spiral shaped portion 51, the distal-end side base 27 and the pipe 28 for bonding them into the inner circumference side of the spiral shaped portion 51. As a result, since the adhesive 32 does not protrude onto the inner circumferential face of the spiral shaped portion 51, the protruding adhesive 32 does not contact the inner cylindrical tube 29 to block rotation during rotation.

Also, at the distal-end side base 27, in a range where the resin coated groove 27c is not provided, in the distal end portion of the spiral shaped portion 51 with respect to the spiral groove 27b, since the resin coating 31 is removed for 1 to 2 spiral pitches, only the distal end portion of the spiral body 30 in the spiral shaped portion 51 is inserted and bonded and fixed.

The distal-end side base 27 and the spiral shaped portion 51 are fixed by the adhesive 32 but as mentioned above, since the spiral body 30 and the inner circumferential face of the distal-end side base 27 are directly bonded and fixed, the adhesion strength is improved as compared with a case through the resin.

The distal-end side base 27 is formed of polysulfone, POM (polypenco acetal), ABS having a high sliding performance and the like so that the base can move smoothly when rotating with respect to the spiral tube connection base 21.

The pipe 28 is fixed to the inner circumference on the distal end side of the spiral shaped portion 51 in the insertion direction S with such a length that it does not protrude to the rear end side in the insertion direction S from the rear end portion of the distal-end side base 27 and specifically, it has a length of 1.5 to 2.0 pitches of the spiral body 30 and is fixed to the inner circumferential face of the distal-end side base 27.

By fixing the pipe 28 on the distal end side of the spiral shaped portion 51, the adhesive 32 bonding the spiral shaped portion 51 and the distal-end side base 27 to each other is prevented from flowing into the inner circumference side of the spiral shaped portion 51. As a result, since the adhesive 32 does not protrude onto the inner circumferential face of the spiral shaped portion 51, contact of the protruding adhesive 32 with the inner cylindrical tube 29 at rotation so as to obstruct rotation of the spiral shaped portion 51 is prevented.

The spiral shaped portion 51 is a rotatable cylindrical body and constitutes a thrust member for generating a force at the insertion portion main body 10 to advance/retreat the insertion portion main body 10 in the intestine by contact with the intestinal wall.

The spiral shaped portion 51 is integrally fixed to the distal-end side base 27 by the adhesive 32. The spiral shaped portion 51 is configured to be rotatable around the axis in the longitudinal direction, which is the insertion direction S, when a torque is given from a motor, not shown, disposed in the above-mentioned motor box 16 (See FIG. 1) through the flexible shaft 33.

The spiral shaped portion 51 is constituted by the spiral body 30 formed by loosely winding a spring material and the resin coating 31 having biocompatibility continuing between lines of the spiral body 30. The resin coating 31 may be either in a mode covering the outer circumference side of the spiral body 30 or in a mode covering the inner circumference side.

The spiral shaped portion 51 is, as shown in FIG. 4, provided in a setting range from the rear end side of the distal-end side base 27 in the insertion direction S. The spiral shaped portion 51 may be provided at a part of the flexible shaft 33, may be provided over the entire length of the flexible shaft 33, or moreover, may be provided discontinuously along the insertion direction S in the flexible shaft 33.

The spiral shaped portion 51 has a sufficient clearance inside so that the resin coating 31 does not interfere with the inner cylindrical tube 29 and the like or press the inner cylindrical tube 29 and the like or the inner cylindrical tube 29 does not rotate with the resin coating 31, caused by interference with the inner cylindrical tube 29 and the like, when the spiral shaped portion 51 is bent to the utmost degree.

The flexible shaft 33 has flexibility capable of being inserted into an intestine and good torque transmission from the motor, not shown, disposed in the motor box 16 and is coated with a resin having good sliding performance with the intestinal wall and biocompatibility on the outer circumferential face.

The distal end side of the flexible shaft 33 in the insertion direction S is integrally connected to the spiral shaped portion 51, while the rear end side in the insertion portion S is connected to the motor, not shown, in the motor box 16. Thus, the flexible shaft 33 gives a torque from the motor to the spiral shaped portion 51. The flexible shaft 33 may be in configuration such as three-layer densely wound coil and the like in which coils wound to the right, left and right are laminated from an inner layer to an outer layer, for example, in order to improve the torque transmission.

Next, configuration of the suction pressure controller 4 will be described referring to FIG. 7. As shown in FIG. 7, the suction pressure controller 4 has the essential part constituted by the suction bin 71, a connection tube 73, a suction pump 74, a pressure sensor 75, a suction pressure control portion 76, a suction-pump signal cable 77, and a pressure-sensor signal cable 78.

To the suction bin 71, the other end side of the suction tube 4a in the insertion direction S is connected, and in the suction bin 71, a suctioned substance 72 such as body fluid and the like in the intestine suctioned from the suction opening portion 24 through the suction tube 4a is reserved.

The connection tube 73 is a tube for connecting the suction pump 74 and the suction bin 71 to each other. The suction pump 74 suctions air, liquid and the like in the intestine through the suction tube 4a, the suction bin 71, the connection tube 73 and the like. The suction pump 74 is connected to the suction pressure control portion 76 through the suction-pump signal cable 77 in configuration that a suction pressure is controlled by the suction pressure control portion 76.

The pressure sensor 75 is disposed so that a measurement portion 75s is located in the suction bin 71. The pressure sensor 75 is connected to the suction pressure control portion 76 through the pressure-sensor signal cable 78 and transmits a signal of a pressure in the suction bin 71 to the suction pressure control portion 76.

Next, an action of the present embodiment configured as above will be described using FIG. 8 together with the above-mentioned FIGS. 1 to 7. FIG. 8 is a diagram schematically illustrating the distal end side in the insertion direction of the insertion portion main body in FIG. 4 in a state inserted into the intestine.

First, the insertion portion main body 10 before use is contained in a looped state in the above-mentioned insertion portion container case 12. When an examination or treatment is to be conducted using the endoscope 2, first, an operator inserts an insertion assisting tool 11 from an anus of a patient lying on a bed.

At this time, by bringing the contact portion 11a of the insertion assisting tool 11 into contact with buttocks of the anus of the patient, only an insertion tube on the distal end side of the insertion assisting tool 11 is inserted into a rectum through the anus, and insertion of the entire insertion assisting tool 11 into the rectum is prevented. In this state, the operator fixes the entire circumference of the contact portion 11a to the buttocks of the patient with a tape and the like. By fixing the entire circumference of the contact portion 11a as above, air in the body is prevented from leaking from the anus.

Then, the operator pushes the insertion portion main body 10 into a position where the spiral shaped portion 51 is in contact with the intestinal wall 100 through the insertion assisting tool 11. At this time, in order to recognize a lumen direction in the intestine, the operator feeds air from an opening of the air/water supply pipeline formed at the distal end portion 8 by a predetermined operation such as an operation at hand of the remote controller 67 and the like so as to inflate the inside of the intestine.

As a result, if inflation of the inside of the intestine is not confirmed from an endoscopic image in the monitor 3a, there is a possibility that an air-tightness keeping member 19 is damaged. Thus, in this case, first, the insertion assisting tool 11 and the insertion portion main body 10 are pulled out of the anus and the air-tightness keeping member 19 provided at the distal end of the insertion assisting tool 11 is removed.

After that, the insertion assisting tool 11 and the distal-end side guide tube 13 are disassembled, one of air-tightness keeping member spares 19a provided at the small diameter portion 13a of the distal-end side guide tube 13 is removed, and the removed air-tightness keeping member spare 19a is placed over the distal end portion of the insertion assisting tool 11. That is, the air-tightness keeping member 19 is replaced. The replacement work may be conducted when damage on the air-tightness keeping member 19 is noticed before insertion.

After that, the operator conducts the predetermined operation such as the operation at hand of the operation switch 68 on the remote controller 67 so as to rotate the spiral shaped portion 51 provided at the insertion portion main body 10 in a direction where the spiral shaped portion 51 around the longitudinal axis is advanced.

Specifically, the motor, not shown, disposed in the motor box 16 of the endoscope 2 is brought into a rotated and driven state by the operation at hand of the operation switch 68 on the remote controller 67, by which a torque is transmitted to the flexible shaft 33 by rotation of the motor and moreover, the torque is transmitted from the rear end side to the distal end side in the insertion direction S of the flexible shaft 33. The distal end side of the flexible shaft 33 is integrally connected to the spiral shaped portion 51, and as a result, the torque is transmitted to the spiral shaped portion 51.

When the spiral shaped portion 51 is rotated in contact with the intestinal wall 100, a contact state between the spiral shaped portion 51 and the intestinal wall 100 becomes a relation between a male screw and a female screw, and the spiral shaped portion 51 obtains a thrust from the intestinal wall. That is, the spiral shaped portion 51 is advanced by the thrust generated by contact with the intestinal wall.

At this time, the distal-end side base 27 fixed to the distal end portion of the spiral shaped portion 51 in the insertion direction S is brought into contact with the spiral tube connection base 21 while being rotated in engagement with the engagement portion 21a and presses the spiral tube connection base 21, that is, the bending portion 9. As a result, the entire insertion portion main body 10 including the distal end portion 8 and the bending portion 9 is advanced toward the depth in the intestine. At this time, the distal end portion 8, the bending portion 9, and the spiral tube connection base 21 are advanced along the insertion direction S without being accompanied with rotation.

Here, in the endoscopic image displayed on the monitor 3a at insertion of the insertion portion main body 10, if the operator confirms that the distal end portion 8 has not been advanced, the operator conducts an operation to inflate the balloon 17 by the operation at hand of the remote controller 67 and the like.

Specifically, when the operation switch 68 of the remote controller 67 is operated, a fluid fed out of the fluid supply device, not shown, in the in-balloon controller 7 is supplied into the balloon 17 by the in-balloon fluid supply hole 22 through the in-balloon fluid supply tube 7a and the L-shaped pipe 23 for balloon, by which the balloon 17 is inflated. Timing to inflate the balloon 17 is not limited to a case where it is confirmed that the distal end portion 8 has not been advanced but may be immediately after insertion start of the insertion portion main body 10, for example.

Also, as mentioned above, since the pressure sensor, not shown, is disposed in the in-balloon controller 7 in order to monitor a pressure of the fluid to be supplied, the operator can confirm the contact state between the balloon 17 and the intestinal wall 100 by a value indicated by the pressure sensor.

Moreover, the in-balloon controller 7 controls a fluid pressure supplied by the in-balloon controller 7 so that the balloon 17 does not excessively push open the intestinal wall 100. At this time, the spiral shaped portion 51 may be in the rotated state or in the rotation stopped state.

After the balloon 17 is brought into contact with the intestinal wall 100, the operator conducts the predetermined operation such as the operation at hand of the operation switch 68 on the remote controller 67 and the like so as to conduct suction of air and the like in the intestine from the suction opening portion 24 formed between the balloon 17 and the spiral shaped portion 51.

Specifically, by the operation of the operation switch 68 on the remote controller 67 by the operator, the suction pump 74 in the suction pressure controller 4 is operated, and air and the like in the intestine is suctioned from the suction opening portion 24 between the spiral shaped portion 51 and the balloon 17 through the connection tube 73, the suction bin 71, the suction tube 4a, and the L-shaped pipe 25 for suction.

When the air and the like in the intestine is suctioned, as shown in FIG. 8, the diameter of the intestine on the rear end side in the insertion direction S from the balloon 17 is reduced, and the entire outer circumferential face of the spiral shaped portion 51 is strongly brought into contact with the intestinal wall 100. By strong contact of only the spiral shaped portion 51 with the intestinal wall 100, as compared with a usual contact state when suction is not carried out from the suction opening portion 24, specifically, a state where a part of the spiral shaped portion 51 is in contact with the intestinal wall 100, the thrust by the spiral shaped portion 51 is extremely increased.

Here, if the suction from the suction opening portion 24 becomes too strong, the intestinal wall 100 is sucked to the suction opening portion 24, which might prevent thrust. In order to prevent that from occurring, the suction pressure from the suction opening portion 24 is controlled by the suction pressure controller 4.

In the suction pressure controller 4, the pressure sensor 75 is installed so that a pressure in the suction bin 71 that recovers the suctioned substance 72 from the suction opening portion 24 can be measured by the measurement portion 75s, and a pressure measured value in the suction bin 71 is transmitted to the suction pressure control portion 76 by the pressure-sensor signal cable 78.

The suction pressure control portion 76 calculates a suction pressure of the suction pump 74 so that the pressure in the suction bin 71 does not fall under a predetermined value and controls the suction pressure of the suction pump 74 through the suction-pump signal cable 77. As a result, the suction from the suction opening portion 24 does not become too strong.

Also, as the insertion portion main body 10 is propelled in the intestine, the balloon 17 is not rotated around the axis in the longitudinal direction, which is the insertion direction S, and closure of the lumen in front of the balloon 17 and blockage of insertion of the insertion portion main body 10 by twisting of the intestine by the balloon 17 can be prevented. The inflation of the balloon 17 and suction operation from the suction opening portion 24 after the insertion portion main body 10 has been inserted into the intestine may be conducted all the time or may be conducted arbitrarily by the operator depending on an insertion state of the insertion portion main body 10.

Moreover, in a state where the balloon 17 is inflated and suctioned from the suction opening portion 24, if a fluid is fed from the opening of the air/water supply pipeline formed at the distal end portion 8, the fluid is not fed to the rear end side in the insertion direction S than the balloon 17, and inside the body cavity on the distal end side in the insertion direction S than the distal end portion 8 can be surely inflated, and a favorable observation view can be ensured.

As a result, when the bending portion 9 bends, the intestinal wall does not obstruct, and even with a small bending force to the bending portion 9, the bending portion 9 can be bent. Also, the fluid supply from the opening of the air/water supply pipeline formed at the distal end portion 8 can inflate the lumen even with a small amount of supply, which has a merit that the lumen direction can be grasped easily.

Moreover, as mentioned above, even if the spiral shaped portion 51 is rotated, the distal end portion 8, the bending portion 9 and the spiral tube connection base 21 are not rotated, and when the insertion portion main body 10 is propelled, the circumferential direction of the distal end portion 8 is not changed even if the bending portion 9 is bent.

As mentioned above, in the present embodiment, at the distal end side of the insertion portion main body 10 in the insertion direction S, the suction opening portion 24 is formed between the balloon 17 and the spiral shaped portion 51. Specifically, the suction opening portion 24 is shown to be formed between the balloon 17 and the spiral shaped portion 51 on the distal end side in the insertion direction S than the spiral shaped portion 51.

According to the above, in a state where the balloon 17 is inflated and the balloon 17 is brought into contact with the intestinal wall 100, by suctioning air and the like in the intestine from the suction opening portion 24 in the vicinity of the spiral shaped portion 51 in the rear of the insertion direction S than the balloon 17, only the spiral shaped portion 51 is surely brought into contact with the intestinal wall 100 and the spiral shaped portion 51 can sufficiently obtain the thrust from the intestinal wall 100.

Also, since the suction pressure from the suction opening portion 24 is controlled by the suction pressure controller 4, such an event will not occur that the suction from the suction opening portion 24 becomes too strong and the intestinal wall 100 is sucked to the suction opening portion 24, which obstructs the thrust of the spiral shaped portion 51. That is, the spiral shaped portion 51 is in contact with the intestinal wall 100 with an appropriate pressure.

Moreover, in the present embodiment, in a state where the balloon 17 is inflated and the balloon 17 is brought into contact with the intestinal wall 100, by feeding the fluid from the opening of the air/water supply pipeline of the distal end portion 8, the bending operation of the bending portion 9 or ensuring of the lumen in front in the insertion direction S than the balloon 17 can be carried out easily.

As a result, when the insertion portion main body 10 is inserted into a colon, the distal end portion 8 can be easily made to reach an appendix. Also, since the spiral shaped portion 51 can obtain sufficient thrust with a small motor torque, size increase of the endoscope device 1 can be prevented.

As mentioned above, by bringing only the spiral shaped portion 51 into contact with the intestinal wall 100 surely with an appropriate pressure so as to generate a sufficient thrust at the insertion portion main body 10 and by facilitating recognition of the observation direction in the intestine after the insertion, the rotary self-propelled endoscope 2 with improved insertion performance of the insertion portion main body 10 can be provided.

Second Embodiment

Figure 9:
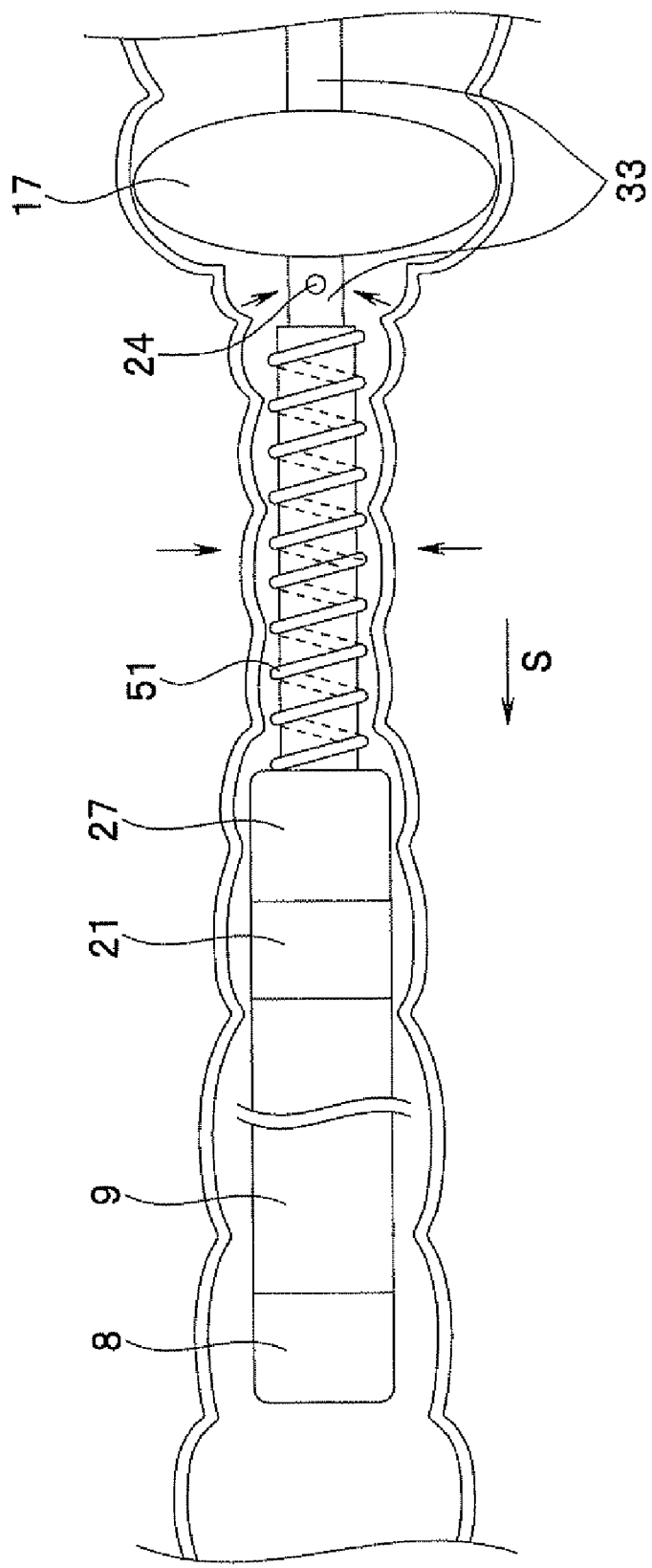
FIG. 9 is a diagram schematically illustrating the distal end side in the insertion direction of the insertion portion main body of the rotary self-propelled endoscope showing a second embodiment in a state inserted into an intestine.

FIG. 9 is a diagram schematically illustrating a state where the distal end side in the insertion direction of the insertion portion main body of the rotary self-propelled endoscope showing the present embodiment is inserted into an intestine.

Configuration of the endoscope of the second embodiment is different from the endoscope in the first embodiment shown in FIGS. 1 to 8 in a point that the suction opening portion is formed on the rear end side in the insertion direction S than the spiral shaped portion. Thus, only the difference will be explained, the same reference numerals are given to the similar configuration in the first embodiment, and the description will be omitted.

As shown in FIG. 9, in the present embodiment, the balloon 17 is provided on the outer circumferential face on the distal end side of the flexible shaft 33 by an adhesive, not shown, or thread winding plus adhesion. Thus, the balloon 17 in the present embodiment is configured to be rotated with the flexible shaft 33.

On the outer circumferential face of the balloon 17, treatment such as hydrophilic lubrication treatment and the like is applied in order to reduce frictional resistance with the intestinal wall 100 so that the intestinal wall 100 is not twisted when the balloon 17 is rotated in contact with the intestinal wall 100.

Moreover, in the embodiment, one or more of the suction opening portion 24 is provided between the balloon 17 and the spiral shaped portion 51 on the outer circumferential face of the flexible shaft 33. Specifically, the suction opening portion 24 is provided in one or more in the rear in the insertion direction S than the spiral shaped portion 51 and in front in the insertion direction S than the balloon 17. The other configurations are the same as those in the first embodiment.

Next, action of the embodiment configured as above will be described.

First the operator inflates the balloon 17 and brings the balloon 17 into contact with the intestinal wall 100 by a predetermined operation at the same timing as in the first embodiment and then, carries out an operation to suction air in the intestine from the suction opening portion 24.

As a result, as shown in FIG. 9, the diameter of the intestine on the distal end side in the insertion direction S than the balloon 17 is reduced and only the entire outer circumferential face of the spiral shaped portion 51 is brought into strong contact with the intestinal wall 100. Since only the spiral shaped portion 51 is brought into strong contact with the intestinal wall 100, the thrust by the spiral shaped portion 51 is remarkably increased as compared with a usual contact state when suctioning from the suction opening portion 24 is not carried out or specifically, a state where a part of the spiral shaped portion 51 is in contact with the intestinal wall 100. At this time, the flexible shaft 33 on the rear end side in the insertion direction S than the balloon 17 is not in strong contact with the intestinal wall 100, and the contact resistance will not become large.

Also, the balloon 17 is rotated with the flexible shaft 33, but since the sliding performance on the outer circumferential face of the balloon 17 is sufficiently good, closure of the lumen in front by the balloon 17 due to twisting of the intestine, which obstructs the insertion, will not occur.

As mentioned above, in the present embodiment, on the distal end side of the insertion portion main body 10 in the insertion direction S, the suction opening portion 24 is shown to be formed between the balloon 17 and the spiral shaped portion 51. Specifically, the suction opening portion 24 is formed between the balloon 17 and the spiral shaped portion 51 on the rear end side in the insertion direction S than the spiral shaped portion 51.

According to the above, in a state where the balloon 17 is inflated and the balloon 17 is brought into contact with the intestinal wall 100, strong contact of the flexible shaft 33 with the intestinal wall 100 so as to make a resistance against propelling of the spiral shaped portion 51 is prevented and since only the spiral shaped portion 51 is surely brought into contact with the intestinal wall 100, the spiral shaped portion 51 can sufficiently obtain the thrust from the intestinal wall 100. Thus, the motor in the motor box 16 can be made smaller than that of the first embodiment. The other effects are the same as those in the first embodiment.

Third Embodiment

Figure 10:
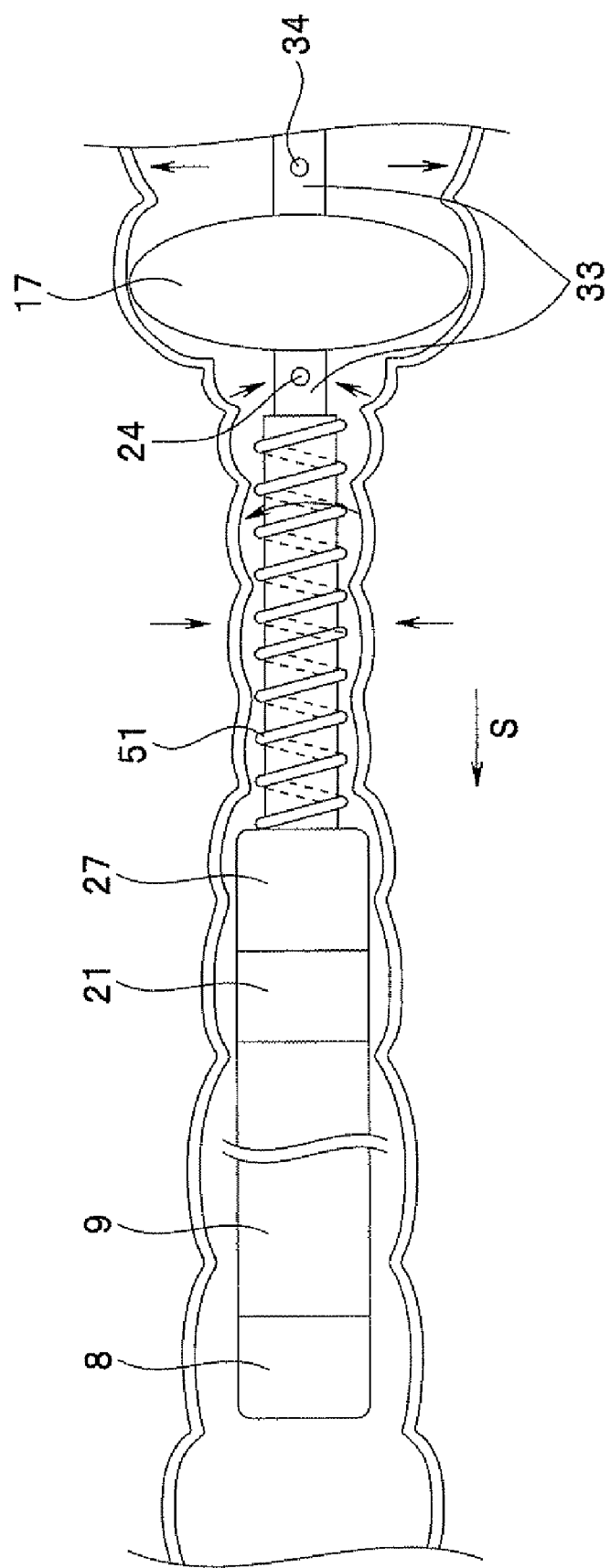
FIG. 10 is a diagram schematically illustrating the distal end side in the insertion direction of the insertion portion main body of the rotary self-propelled endoscope showing a third embodiment in a state inserted into an intestine.

FIG. 10 is a diagram schematically illustrating the distal end side in the insertion direction of the insertion portion main body of the rotary self-propelled endoscope showing the present embodiment being inserted into the intestine.

Configuration of the endoscope of the third embodiment is different from the endoscope in the second embodiment shown in FIG. 9 in a point that the air supply opening portion is formed on the further rear end side in the insertion direction S than the balloon. Thus, only the difference will be explained, the same reference numerals are given to the similar configuration in the second embodiment, and the description will be omitted.

As shown in FIG. 10, in the present embodiment, on the outer circumferential face of the flexible shaft 33, one or more air supply opening portions 34 are provided on the rear end side in the insertion direction S than the balloon 17.

The air supply opening portion 34 is connected to the second controller 54 (See FIG. 1) through an L-shaped pipe for air supply, not shown, and an air supply tube constituting an air supply pipeline so that carbon dioxide is supplied to the air supply opening portion 34 from a carbon dioxide ($CO_2$) tank 57 (See FIG. 1).

Next, an action of the present embodiment configured as above will be described.

First, when the operator carries out a predetermined operation by an operation at hand of the remote controller 67 and the like and carbon dioxide is supplied from the air supply opening portion 34, the intestinal wall 100 on the rear end side in the insertion direction S than the balloon 17 is inflated and as shown in FIG. 10, the flexible shaft 33 on the rear end side in the insertion direction S than the balloon 17 and the intestinal wall 100 are surely separated.

As mentioned above, according to the embodiment, strong contact between the flexible shaft 33 and the intestinal wall 100 to become a resistance to thrust can be prevented more surely than the second embodiment, and the spiral shaped portion 51 can sufficiently obtain the thrust from the intestinal wall 100 similarly to the second embodiment. Thus, the size of the motor in the motor box 16 can be made smaller than that of the second embodiment. Also, the bending operation of the bending portion 9 or ensuring of the lumen can be carried out more easily. The other effects are the same as those in the second embodiment.

Fourth Embodiment

Figure 11:
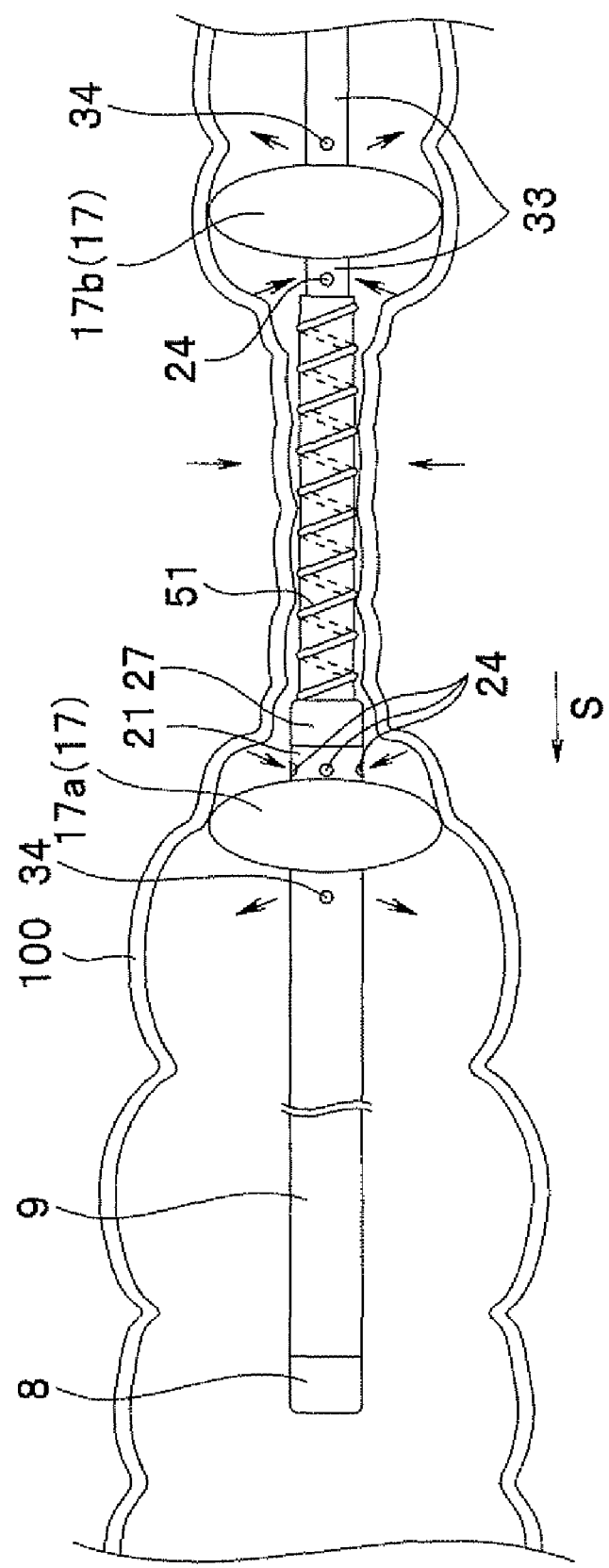
FIG. 11 is a diagram schematically illustrating the distal end side in the insertion direction of the insertion portion main body of the rotary self-propelled endoscope showing a fourth embodiment in a state inserted into an intestine.

FIG. 11 is a diagram schematically illustrating the distal end side in the insertion direction of the insertion portion main body of the rotary self-propelled endoscope showing the present embodiment in a state inserted in the intestine.

Configuration of the endoscope in the fourth embodiment is different from the endoscope in the third embodiment shown in FIG. 10 in a point that a balloon, a suction opening portion and an air supply opening portion are further formed at the spiral tube connection base. Thus, only the difference will be explained, the same reference numerals are given to the similar configuration in the third embodiment, and the description will be omitted.

As shown in FIG. 11, in the present embodiment, the balloon 17 is provided both on the outer circumferential face on the distal end side than the suction opening portion 24 in the insertion direction S of the spiral tube connection base 21 and on the outer circumferential face on the rear end side than the suction opening portion 24 in the insertion direction S of the flexible shaft 33 by an adhesive or thread winding and adhesion.

In the present embodiment, of the balloon 17, the balloon 17 provided at the spiral tube connection base 21 is referred to as a first balloon 17a, which is a first contact member located on the most distal end side and the balloon 17 provided at the flexible shaft 33 is referred to as a second balloon 17b located on the rearmost end side.

A location where the first balloon 17a is provided may be anywhere as long as it is on the distal end side in the insertion direction S than the spiral shaped portion 51, and a location where the second balloon 17b is provided may be anywhere as long as it is on the rear end side in the insertion direction S than the spiral shaped portion 51.

In the embodiment, the suction opening portion 24 is formed at the spiral tube connection base 21 between the first balloon 17a and the spiral shaped portion 51 and at the flexible shaft 33 between the second balloon 17b and the spiral shaped portion 51.

The suction opening portion 24 may be formed only at either one of the spiral tube connection base 21 and the flexible shaft 33 or may be formed in plural at either one of the spiral tube connection base 21 and the flexible shaft 33. Moreover, the suction opening portion may be formed in plural both at the spiral tube connection base 21 and the flexible shaft 33.

One or more air supply opening portion 34 are formed at the spiral tube connection base 21 on the distal end side in the insertion direction S than the first balloon 17a and formed on the outer circumferential face of the flexible shaft 33 on the rear end side in the insertion direction S than the second balloon 17b.

Next, an action of the embodiment configured as above will be described.

By the predetermined operation by the operator, the first balloon 17a and the second balloon 17b are inflated and the first balloon 17a and the second balloon 17b are brought into contact with the intestinal wall 100 and then, by the further predetermined operation by the operator, suctioning is carried out from each suction opening portion 24. Then, as shown in FIG. 11, the diameter of a part of the intestine held between the first balloon 17a and the second balloon 17b is reduced, and the entire outer circumferential face of the spiral shaped portion 51 is brought into strong contact with the intestinal wall 100. Since only the spiral shaped portion 51 is in strong contact with the intestinal wall 100, the thrust by the spiral shaped portion 51 is remarkably increased as compared with a usual contact state where suctioning is not carried out from the suction opening portion 24 or specifically, a part of the spiral shaped portion 51 is in contact with the intestinal wall 100.

The suctioning to bring the spiral shaped portion 51 into contact with the intestinal wall 100 is carried out from the plurality of suction opening portions 24 provided at the spiral tube connection base 21 and the suction opening portion 24 provided at the flexible shaft 33.

Here, in the suction opening portion 24 provided at the spiral tube connection base 21, suctioning is conducted from the plurality of opening portions because if suctioning is conducted from only one suction opening portion 24, a single portion of the intestinal wall 100 is suctioned in a centralized manner, and the intestinal wall 100 is sucked to the suction opening portion 24, which might cause a resistance to the insertion of the insertion portion main body 10. However, if suctioning is conducted from the plurality of suction opening portions 24, the inside of the body cavity can be sufficiently suctioned even with a low pressure, and the intestinal wall 100 becomes less liable to be sucked to the suction opening portion 24.

Though details will be described later in FIG. 18, by making a shape of the suction opening portion 24 in an elongated shape along the outer circumferential direction of the insertion portion main body 10, even if only one suction opening portion 24 is formed at the spiral tube connection base 21, the effect equivalent to formation in plural can be obtained. In this case, the manufacturing costs can be reduced than the formation in plural.

Also, by conducting suctioning also from the suction opening portion 24 formed at the flexible shaft 33, only the spiral shaped portion 51 is brought into contact with the intestinal wall 100 more surely.

With the suctioning from the suction opening portion 24, the operator carries out the predetermined operation such as the operation at hand of the remote controller 67 so as to supply carbon dioxide from each air supply opening portion 34, by which the distal end portion 8 and the bending portion 9 on the distal end side in the insertion direction S than the first balloon 17a are surely separated from the intestinal wall 100, and the flexible shaft 33 on the rear end side in the insertion direction S than the second balloon 17b is also separated from the intestinal wall 100 surely.

As a result, even if the insertion portion main body 10 is inserted into the depth in the intestine, the contact resistance between the portions other than the spiral shaped portion 51 in the insertion portion main body 10 and the intestinal wall 100 will not become large. That is, only the spiral shaped portion 51 is brought into contact with the intestinal wall 100.

Also, as compared with the air supply only from the opening of the air/water supply pipeline of the distal end portion 8, the inside of the body cavity on the distal end side in the insertion direction S than the first balloon 17a can be inflated surely. As a result, since the intestinal wall 100 and the like do not stand in the way when the bending portion 9 bends, the bending portion 9 can be surely bent even with a small bending force. Also, the lumen can be inflated even with a small quantity of air supply. Thus, the lumen direction becomes easier to be grasped.

As mentioned above, in the present embodiment, the first balloon 17a and the second balloon 17b are provided so as to hold the spiral shaped portion 51 between them, and the suction opening portions 24 are shown to be formed between the first balloon 17a and the spiral shaped portion 51 and between the second balloon 17b and the spiral shaped portion 51, respectively. Moreover, on the distal end side of the first balloon 17a in the insertion direction S and the rear end side of the second balloon 17b in the insertion direction S, the air supply opening portions 34 are shown to be formed, respectively.

According to the above, only the spiral shaped portion 51 can be brought into contact with the intestinal wall 100 more surely, and since the portions other than the spiral shaped portion 51 can be brought into strong contact with the intestinal wall 100, the contact resistance between the insertion portion main body 10 and the intestinal wall 100 can be minimized, and the spiral shaped portion 51 can sufficiently obtain the thrust from the intestinal wall 100.

Also, since the sucking between the intestinal wall 100 and the suction opening portion 24 caused by suctioning can be surely prevented, the insertion performance of the insertion portion main body 10 can be improved. Moreover, since air can be supplied not only from the distal end opening of the air/water supply pipeline in the distal end portion 8 but also from the air supply opening portion 34 provided on the distal end side in the insertion direction S than the first balloon 17a, the bending operation and ensuring of the lumen can be carried out more easily. The other effects are the same as those in the third embodiment.

Fifth Embodiment

Figure 12:
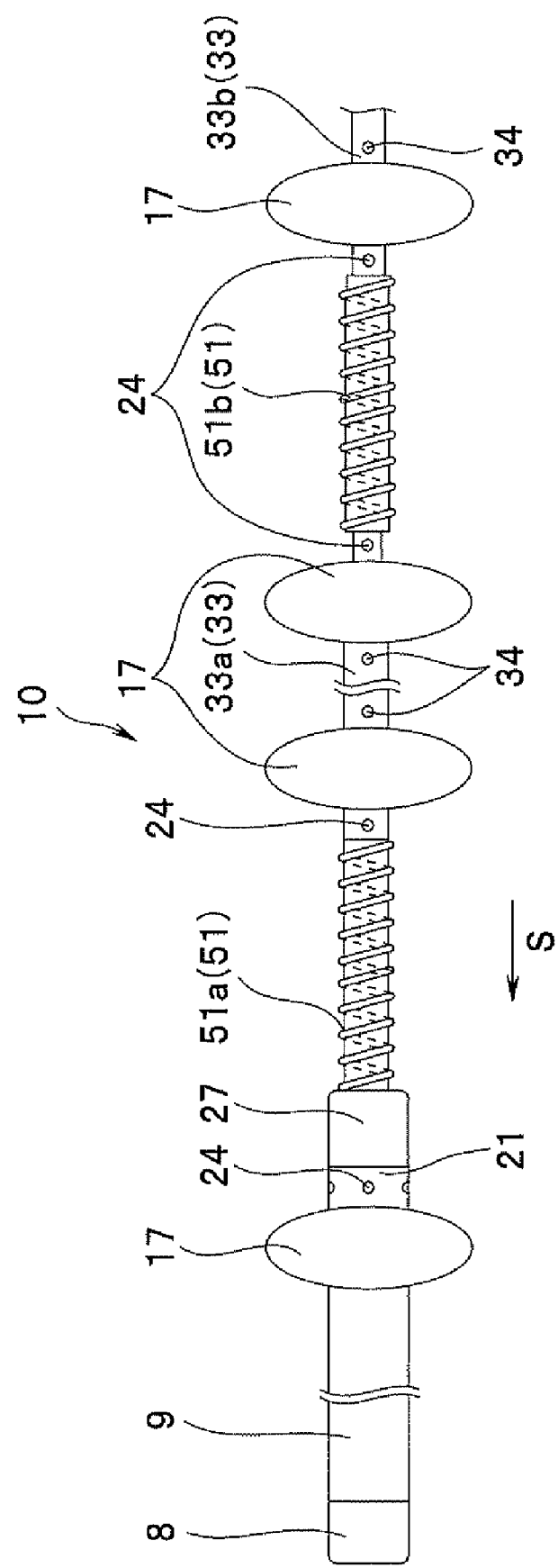
FIG. 12 is a partially enlarged plan view of the distal end side in the insertion direction of the insertion portion main body of the rotary self-propelled endoscope showing a fifth embodiment.

FIG. 12 is a partially enlarged plan view on the distal end side in the insertion direction of the insertion portion main body in the rotary self-propelled endoscope of the present embodiment.

Configuration of the endoscope in the fifth embodiment is different from the endoscope in the fourth embodiment shown in FIG. 11 in a point that two spiral shaped portions are formed adjacently with a predetermined interval along the insertion direction S and the balloon, the suction opening portions, and the air supply opening portions are formed in plural according to the spiral shaped portion. Thus, only the difference will be explained, the same reference numerals are given to the similar configuration in the fourth embodiment, and the description will be omitted.

As shown in FIG. 12, in the present embodiment, of the spiral shaped portion 51, a first spiral shaped portion 51a is connected to the rear end side of the distal-end side base 27 in the insertion direction S and a second spiral shaped portion 51b of the spiral shaped portion 51 is connected to the rear end side of the flexible shaft 33a connected to the rear end side of the first spiral shaped portion 51a in the insertion direction S. The number of spiral shaped portions 51 is not limited to two but may be provided in plural at the insertion portion main body 10.

Also, in the present embodiment, the balloons 17 are provided at plural locations on the outer circumferential face on the distal end side than the suction opening portion 24 in the insertion direction S of the spiral tube connection base 21 and on the outer circumferential face of the flexible shaft 33a along the insertion direction S, respectively, by an adhesive or thread winding plus adhesion. Specifically, the balloons 17 are provided in plural so as to hold therebetween the first spiral shaped portion 51a along the insertion portion S and moreover, so as to hold therebetween the second spiral shaped portion 51b along the insertion portion S.

Moreover, at the spiral tube connection base 21, the flexible shaft 33a, the flexible shaft 33b, the suction opening portion 24 is formed between the balloon 17 and the spiral shaped portion 51. The suction opening portion may be provided in plural at a single location.

The flexible shaft 33a is provided between the first spiral shaped portion 51a and the second spiral shaped portion 51b and also provided on the rear end side of the second spiral shaped portion 51b in the insertion direction S.

The air supply opening portion 34 is provided between the balloons 17 at the flexible shaft 33a provided between the adjacent first spiral shaped portion 51a and the second spiral shaped portion 51b and is also formed at the flexible shaft 33b on the rear end side in the insertion direction S than the second balloon 17 located on the rearmost end side in the insertion direction S.

According to the configuration as above, even in a case such as a patient having an intestine with a long entire length where propelling is getting difficult only with the thrust generated by the first spiral shaped portion 51a provided on the distal end side of the insertion portion main body 10 in the insertion direction S as insertion progresses, since the thrust of the insertion portion main body 10 is remarkably increased when the second spiral shaped portion 51b provided on the rear end side of the first spiral shaped portion 51a in the insertion portion S is inserted into the intestine in the present embodiment, the insertion portion main body 10 is propelled without trouble.

Thus, even if the length of the insertion portion main body 10 to be inserted into the body becomes longer as in the patient with the long intestinal entire length, the sufficient thrust for the distal end side of the insertion portion main body 10 in the insertion direction S to be propelled can be obtained. Therefore, the motor in the motor box 16 can be made smaller than that of the fourth embodiment. The other effects are the same as those in the fourth embodiment.

Sixth Embodiment

Figure 13:
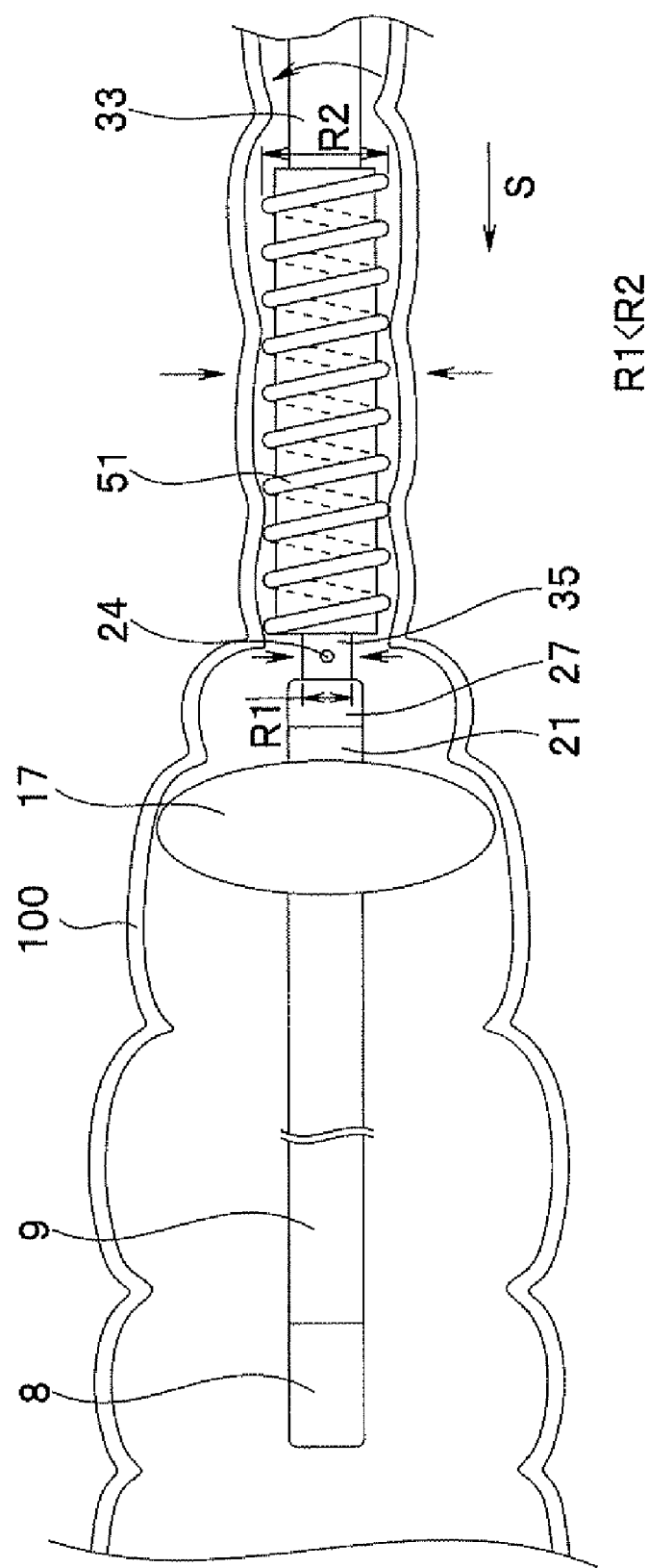
FIG. 13 is a diagram schematically illustrating the distal end side in the insertion direction of the insertion portion main body of the rotary self-propelled endoscope showing a sixth embodiment in a state inserted into an intestine.

FIG. 13 is a diagram schematically illustrating the distal end side in the insertion direction of the insertion portion main body of the rotary self-propelled endoscope shown in the present embodiment in a state inserted into the intestine.

Configuration of the endoscope in the sixth embodiment is different from the endoscope in the first embodiment shown in FIGS. 1 to 8 in a point that the suction opening portion is formed at the base with a diameter smaller than the spiral shaped portion connecting the distal end side base and the spiral shaped portion. Thus, only the difference will be explained, the same reference numerals are given to the similar configuration in the first embodiment, and the description will be omitted.

As shown in FIG. 13, a suction opening portion base 35 having a cylindrical shape is provided between the distal-end side base 27 and the spiral shaped portion 51 so that the cylindrical axis matches the axis of the insertion portion main body 10 in the insertion direction S.

The suction opening portion base 35 is provided between the distal-end side base 27 and the spiral shaped portion 51 by being bonded to the distal-end side base 27 and the spiral shaped portion 51, respectively. Also, an outer diameter R1 of the suction opening portion base 35 is formed smaller than an outer diameter R2 of the spiral shaped portion 51 (R1<R2).

Moreover, at the suction opening portion base 35 formed as above, the suction opening portion 24 is formed.

According to the configuration as above, when suctioning is conducted from the suction opening portion 24, since the intestinal wall 100 is brought into contact with the spiral shaped portion 51 with a larger diameter than the suction opening portion base 35, the intestinal wall 100 is less liable to be sucked to the suction opening portion 24. Thus, insertion of the insertion portion main body 10 is not prevented by suctioning of the suction opening portion 24.

Thus, an endoscope in configuration in which the sucking of the intestinal wall 100 to the suction opening portion 24 so as to become resistance to thrust can be prevented and the spiral shaped portion 51 can sufficiently obtain the thrust from the colon wall can be provided. The other effects are the same as those in the first embodiment.

Seventh Embodiment

Figure 14:
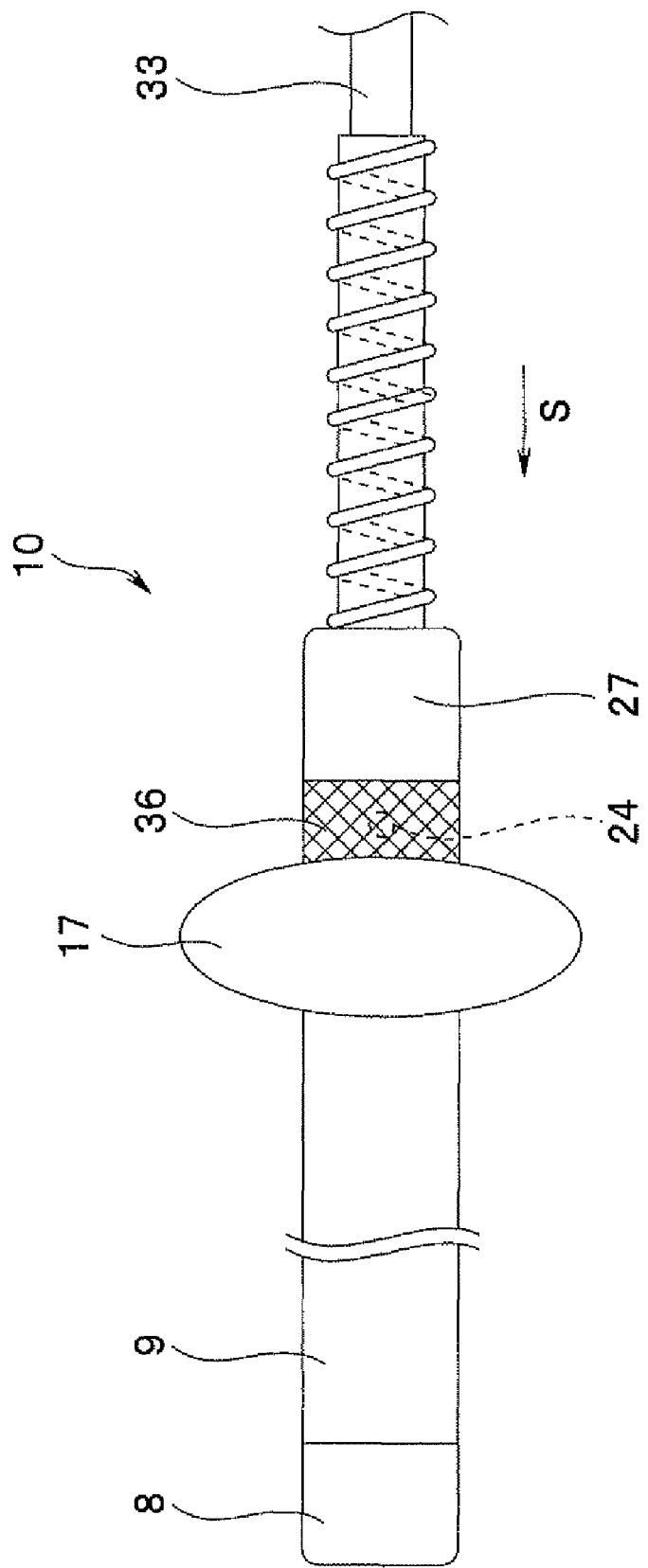
FIG. 14 is a partially enlarged plan view of the distal end side in the insertion direction of the insertion portion main body in the rotary self-propelled endoscope of a seventh embodiment.

FIG. 14 is a partially enlarged plan view of the distal end side in the insertion direction of the insertion portion main body in the rotary self-propelled endoscope of the present embodiment.

Configuration of the endoscope of the seventh embodiment is different from the endoscope of the first embodiment shown in FIGS. 1 to 8 in a point that a sucking preventing member covering the suction opening portion is further provided at the insertion portion main body. Thus, only the difference will be explained, the same reference numerals are given to the similar configuration in the first embodiment, and the description will be omitted.

As shown in FIG. 14, a sucking preventing member 36 constituted by a thin mesh member is provided so as to cover the suction opening portion 24 in the spiral tube connection base 21. The mesh of the sucking preventing member 36 is formed finely to a degree that suctioning from the suction opening portion 24 can be carried out sufficiently so that the intestinal wall 100 does not bite into the sucking preventing member 36 when sucking is carried out from the suction opening portion 24.

According to the above configuration, when suctioning is carried out from the suction opening portion 24, the intestinal wall 100 is brought into contact with the sucking preventing member 36 and since the mesh of the sucking preventing member 36 is sufficiently fine, the intestinal wall 100 is not sucked to the suction opening portion 24 by suctioning from the suction opening portion 24 due to the sucking preventing member 36, and insertion of the insertion portion main body 10 is not hindered.

As a result, the sucking of the intestinal wall 100 to the suction opening portion 24 so as to become the resistance to the propelling of the insertion portion main body 10 can be prevented, and the endoscope in which the spiral shaped portion 51 can sufficiently obtain the thrust from the intestinal wall 100 can be provided. The other effects are the same as those in the first embodiment.

Eighth Embodiment

Figure 15:
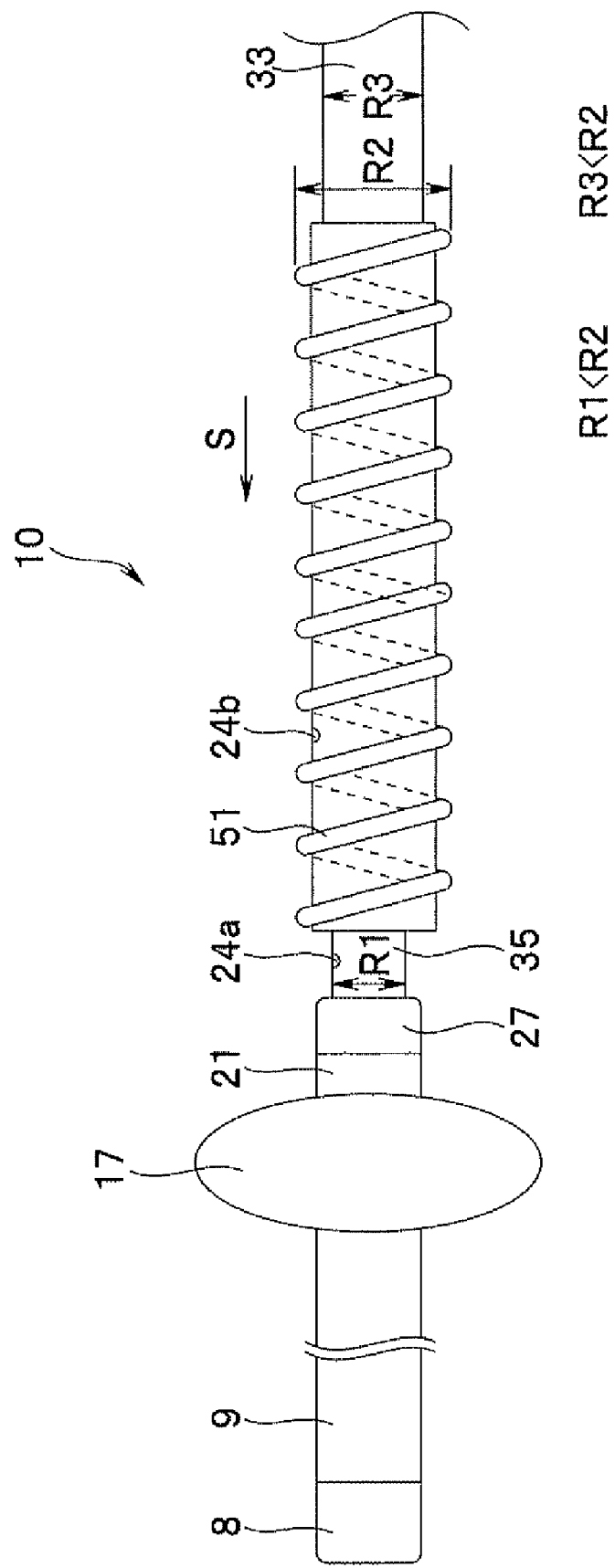
FIG. 15 is a partially enlarged plan view of the distal end side in the insertion direction of the insertion portion main body in the rotary self-propelled endoscope of an eighth embodiment.

FIG. 15 is a partially enlarged plan view of the distal end side in the insertion direction of the insertion portion main body in the rotary self-propelled endoscope of the present embodiment.

Configuration of the endoscope of the eighth embodiment is different from the endoscope of the sixth embodiment shown in FIG. 13 in a point that the suction opening portion is formed at the base with a diameter smaller than that of the spiral shaped portion connecting the distal-end side base and the spiral shaped portion and at the spiral shaped portion and the flexible shaft is formed with a diameter smaller than that of the spiral shaped portion. Thus, only the difference will be explained, the same reference numerals are given to the similar configuration in the sixth embodiment, and the description will be omitted.

As shown in FIG. 15, the suction opening portion base 35 having the above-mentioned outer diameter R1 is formed between the distal-end side base 27 and the spiral shaped portion 51, and at the suction opening portion base 35, a first suction opening portion 24a is formed. The outer diameter R1 of the suction opening portion base 35 is smaller than the outer diameter R2 of the spiral shaped portion 51. The first suction opening portion 24a is connected to the suction tube 4a.

Also, an outer diameter R3 of the flexible shaft 33 is formed smaller than the outer diameter R2 of the spiral shaped portion 51.

At the spiral shaped portion 51 having the outer diameter R3 larger than the outer diameter R1 of the suction opening portion base 35 and larger than the outer diameter R2 of the flexible shaft 33, a second suction opening portion 24b is formed. The second suction opening portion 24b is also connected to the suction tube 4a.

Next, an action of the embodiment configured as above will be described.

When suctioning is carried out from both the two suction opening portions 24a, 24b, the intestinal wall 100 is firstly brought into contact with the spiral shaped portion 51 with the largest outer diameter and then, blocks the second suction opening portion 24b. At this time, the pressure in the suction tube 4a is slightly raised than the case where the opening portion is not blocked by the intestinal wall 100, and a value of the pressure sensor 75 (See FIG. 7) installed at the suction pressure controller 4 is also slightly raised than the case not blocked by the intestinal wall 100.

Since suctioning is being carried out from the second suction opening portion 24b provided at the spiral shaped portion 51, the contact between the spiral shaped portion 51 and the intestinal wall 100 becomes strong.

As mentioned above, gradual increase of the value of the pressure sensor 75 makes the contact state between the intestinal wall 100 and the insertion portion main body 10 easy to grasp and moreover, since the value of the pressure sensor 75 is not rapidly raised, there is no need to expedite a response of control of the suction pressure in the suction pressure control portion 76 and the suction pressure can be easily controlled to an appropriate value.

Even if the suctioning is continued after the spiral shaped portion 51 and the intestinal wall 100 are brought into contact with each other, the rear end side from the spiral shaped portion 51 is not suctioned. Thus, the intestinal wall 100 is not contracted from the outer diameter of the spiral shaped portion 51 and the flexible shaft 33 with a diameter smaller than the spiral shaped portion 51 is not brought into strong contact with the intestinal wall 100. As a result the flexible tube 33 and the intestinal wall 100 are not brought into strong contact with each other or insertion of the insertion portion main body 10 is not prevented.

As mentioned above, the endoscope that can easily control the suction pressure controlled by the suction pressure control portion 76 to an appropriate value can be provided. Also, strong contact between the flexible shaft 33 and the intestinal wall 100 so as to become resistance to the thrust can be prevented more surely than the second embodiment, and the spiral shaped portion 51 can obtain the thrust from the intestinal wall 100 more than in the second embodiment. The other effects are the same as those in the first embodiment.

Ninth Embodiment

Figure 16:
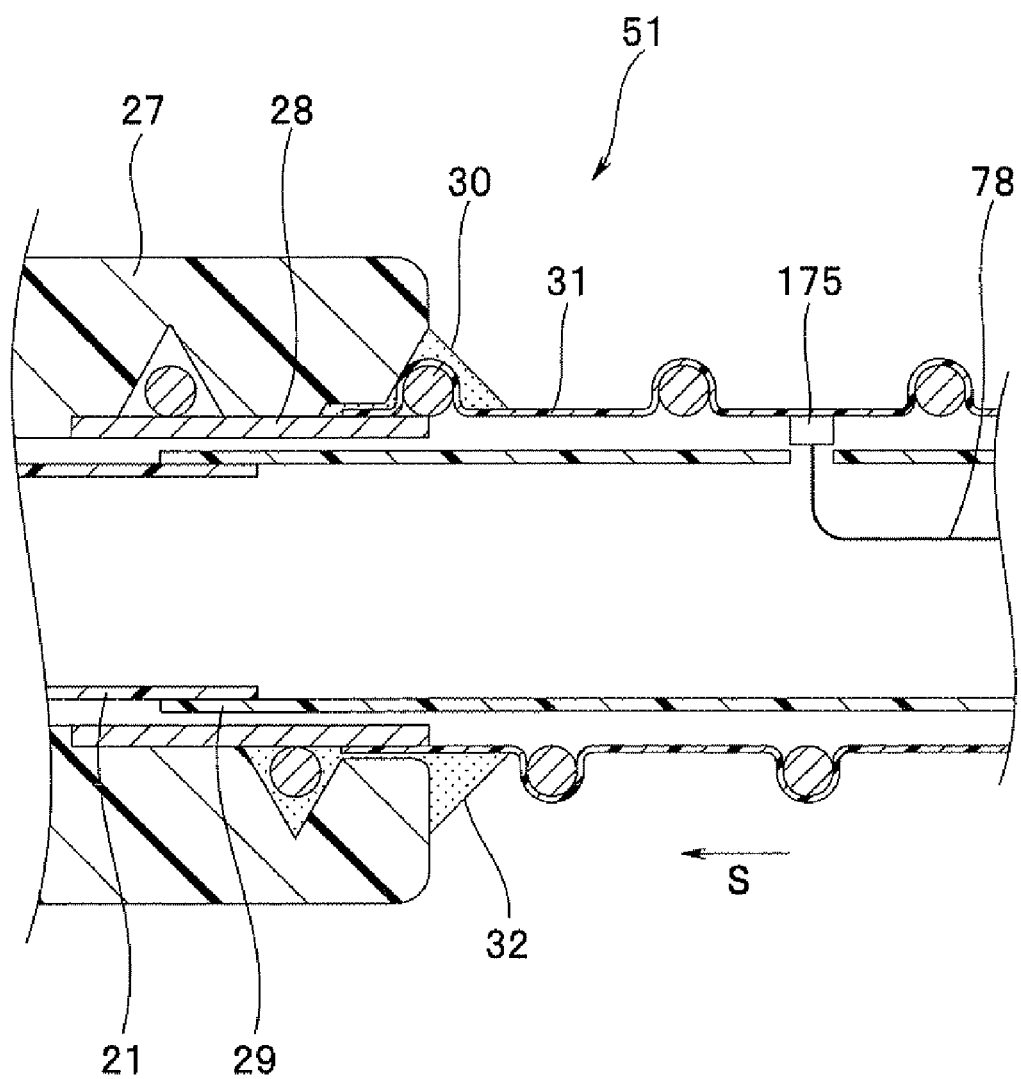
FIG. 16 is a partially enlarged sectional view of the insertion portion main body in the rotary self-propelled endoscope of a ninth embodiment.

FIG. 16 is a partially enlarged sectional view of the insertion portion main body in the rotary self-propelled endoscope of the present embodiment.

Configuration of the endoscope of the ninth embodiment is different from the endoscope of the first embodiment shown in FIGS. 1 to 8 in a point that a contact pressure detecting member for detecting a contact pressure between the spiral shaped portion and a colon wall is provided at the spiral shaped portion. Thus, only the difference will be explained, the same reference numerals are given to the similar configuration in the first embodiment, and the description will be omitted.

As shown in FIG. 16, a pressure sensor 175, which is a contact pressure detecting member is provided on the inner circumference side of the resin coating 31 in the spiral shaped portion 51 so that a measurement portion in the pressure sensor 175 is directed to the outer circumferential direction of the resin coating 31.

The pressure sensor 175 detects a contact pressure with the intestinal wall 100 and transmits the detected value to the suction pressure control portion 76 through the pressure-sensor signal cable 78 (See FIG. 7 for both). After the transmission, on the basis of the detection of the contact pressure by the pressure sensor 175, the suction pressure from the suction opening portion 24 is adjusted by the suction pressure control portion 76.

In the present embodiment, the pressure sensor 175 is provided at the spiral shaped portion 51, but as another example, the sensor may be provided in the balloon 17 and it may be so configured that the contact pressure between the balloon 17 and the intestinal wall 100 is measured using the pressure sensor provided at the balloon 17 so that the suction pressure from the suction opening portion 24 is controlled.

According to the configuration as above, after suctioning is carried out from the suction opening portion 24 and the intestinal wall 100 and the spiral shaped portion 51 are brought into contact with each other, the contact pressure is detected by the pressure sensor 175, and the detected value of the contact pressure is transmitted to the suction pressure control portion 76 through the pressure-sensor signal cable 78.

After that, the suction pressure from the suction opening portion 24 is controlled by the suction pressure control portion 76 so that the contact pressure between the spiral shaped portion 51 and the intestinal wall 100 is kept at a contact pressure with which the spiral shaped portion 51 can obtain sufficient thrust.

From the above, too high contact pressure between the spiral shaped portion 51 and the intestinal wall 100 so as to become the resistance to the propelling of the insertion portion main body 10 can be prevented and the endoscope having a structure where the spiral shaped portion 51 can sufficiently obtain the thrust from the intestinal wall 100 can be provided. The other effects are the same as those in the first embodiment.

Variations will be illustrated below. In the above-mentioned first to ninth embodiments, as the endoscope 2 of the self-propelled type, a rotary self-propelled endoscope having the spiral shaped portion 51 as the thrust of the insertion portion main body 10 was shown as an example, but the first to ninth embodiments can be applied to self-propelled endoscopes provided with a thrust generation portion such as a caterpillar and the first to ninth embodiments can be also applied to the other self-propelled endoscopes other than the rotary self-propelled types.

Also, in the above-mentioned first to ninth embodiments, a case where the insertion portion main body 10 is inserted into a colon has been illustrated as an example, but it is needless to say that the first to ninth embodiments can be applied to a case of insertion to those other than the colon as long as they are tissues in a body cavity.

Also, in the above-mentioned first to ninth embodiments, as the self-propelled endoscope, medical endoscopes are shown as an example, but not being limited thereto, it is needless to say that the present embodiment may be applied to industrial endoscopes. In this case, the self-propelled endoscope has the same effects as those in the first to ninth embodiments when the self-propelled endoscope is inserted into a lumen or particularly into a soft lumen.

Figure 17:
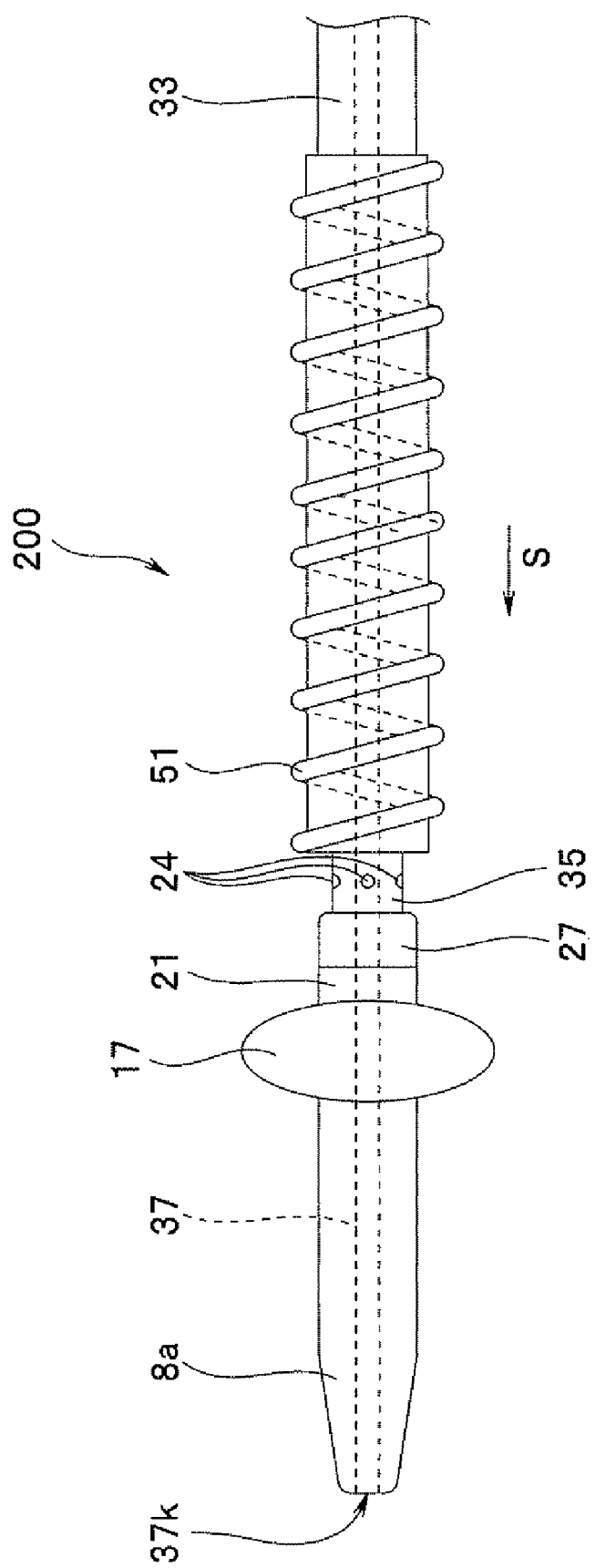
FIG. 17 is a diagram illustrating the distal end side of the insertion portion main body in a rotary self-propelled catheter.

Moreover, a variation of the above-mentioned first to ninth embodiments will be described below using FIG. 17. FIG. 17 is a diagram illustrating the distal end side of the insertion portion main body in a rotary self-propelled type catheter.

In the above-mentioned first to ninth embodiments, a rotary self-propelled endoscope was illustrated as an example of the medical instrument, but not being limited thereto, the above-mentioned first to ninth embodiments may be applied to the rotary self-propelled catheter.

Specifically, as shown in FIG. 17, at the above-mentioned spiral tube connection base 21 on the distal end side in the insertion direction S of the insertion portion main body in a rotary self-propelled catheter 200, the balloon 17 is provided, to the rear end side in the insertion direction S than the above-mentioned distal-end side base 27, the above-mentioned suction opening portion base 35 is connected, and to the rear end side in the insertion direction S than the suction opening portion base 35, the spiral shaped portion 51 is connected.

Also, between the balloon 17 and the spiral shaped portion 51, a plurality of suction opening portions 24 are formed at the suction opening portion base 35 as in the above-mentioned first to ninth embodiments.

Also, on the distal end face of the distal end portion 8 on the distal end side of the insertion portion main body in the insertion direction S, an opening 37k of a liquid feed/discharge pipeline 37 is formed, and using the opening 37k, a drug can be poured into the body cavity or body fluid can be discharged from the body cavity.

By applying the above-mentioned first to ninth embodiments to such catheter 200, too, the similar effects to those of the rotary self-propelled endoscope shown in the above-mentioned first to ninth embodiments can be obtained except the bending operation.

Moreover, the medical instrument is not limited to the above-mentioned endoscope 2 and the catheter 200, the instrument may be of any type as long as it has a self-propelled insertion portion.

Another variation will be illustrated below using FIG. 18. FIG. 18 is a partially enlarged plan view illustrating a variation on the distal end side in the insertion direction of the insertion portion main body in the rotary self-propelled endoscope in FIG. 4.

Figure 18:
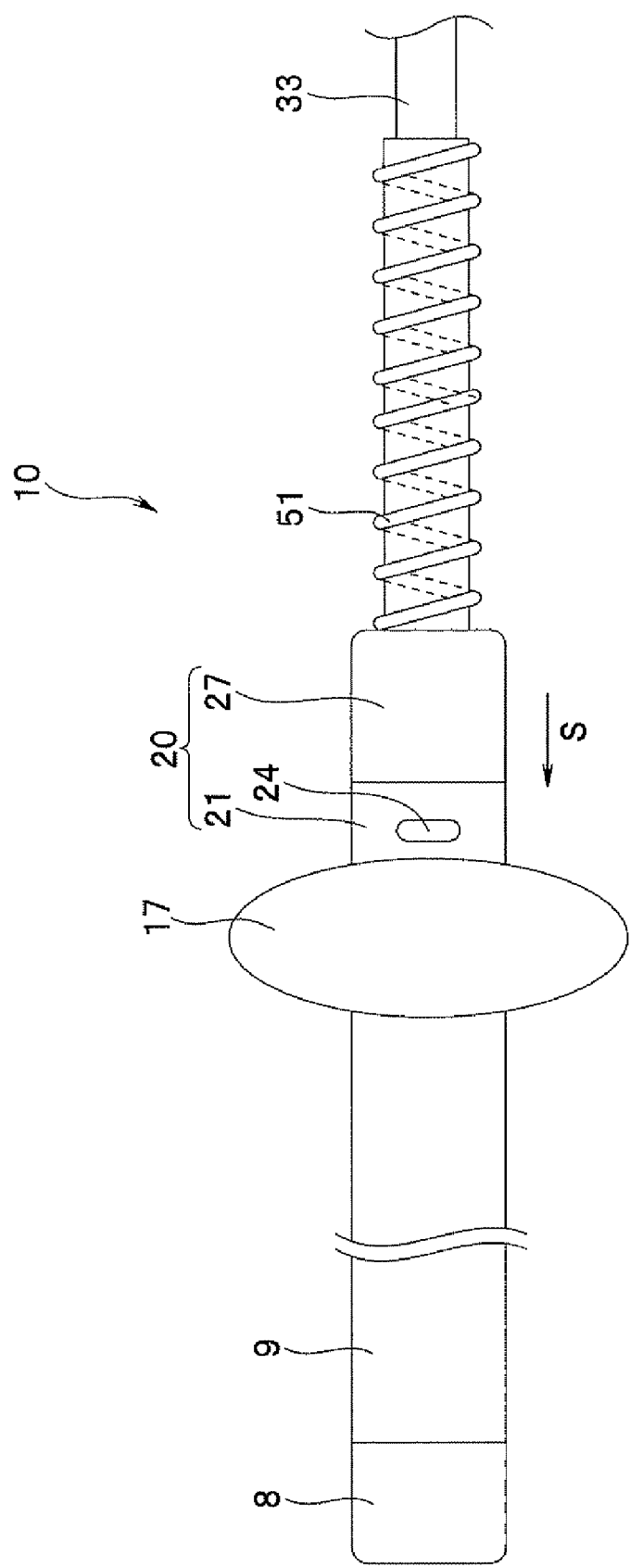
FIG. 18 is a partially enlarged plan view illustrating a variation of the distal end side in the insertion direction of the insertion portion main body in the rotary self-propelled endoscope in FIG. 4.

In the above-mentioned first to ninth embodiments, as shown in FIGS. 1 to 16, the suction opening portion 24 is shown to be formed in a circular shape, but not being limited thereto, as shown in FIG. 18, the suction opening portion 24 may be formed in an elongated shape along the outer circumferential direction of the insertion portion main body 10.

Also, the invention described in the above embodiments is not limited to the embodiments but capable of various variations in a range not departing from its gist when being put into practice. Moreover, the above embodiments include invention in the various stages, and various inventions can be extracted by appropriate combinations in a plurality of disclosed constituent elements.

For example, if the problem described in the problems to be solved by the invention can be solved and the effect described in the advantages of the invention can be obtained even though some of all the constituent elements shown in the embodiments are deleted, the configuration with the constituent elements deleted can be extracted as the invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical instrument comprising:
 a propelling member provided at an insertion portion to be automatically inserted into a subject, for generating a force at the insertion portion to advance/retreat in an insertion direction of the insertion portion in the subject by rotation in contact with a body wall of the subject;
 a contact member provided at a more distal position in the insertion direction than the propelling member in the insertion portion to be capable of inflation/deflation so as to expand radially in a radial direction of the insertion portion, the contact member being capable of contact with the body wall when inflated;
 a suction opening portion provided at a position between the propelling member and the contact member in the insertion direction in the insertion portion, for bringing the propelling member in contact with the body wall at a more proximal position than the contact member in the insertion direction by sucking an atmosphere in the subject at the more proximal position than the contact member in the insertion direction in a state where the contact member is in contact with the body wall; and
 a suction pipeline communicating with the suction opening portion, inserted into the insertion portion and connected to a suction device on a rear end side of the insertion portion in the insertion direction.

2. The medical instrument according to claim 1, wherein the propelling member is provided close to a distal end portion located at a distal end of the insertion portion in the insertion direction.

3. The medical instrument according to claim 1, wherein the contact member is provided on the rear end side in the insertion direction than the propelling member.

4. The medical instrument according to claim 3, further comprising:
 an air supply opening portion provided on the rear end side in the insertion direction than the contact member; and
 an air supply pipeline communicating with the air supply opening portion, inserted into the insertion portion and connected to an air supply device on the rear end side of the insertion portion in the insertion direction.

5. The medical instrument according to claim 1, wherein the contact member is provided both on the distal end side and the rear end side in the insertion direction than the propelling member.

6. The medical instrument according to claim 1, wherein a shaft with a diameter smaller than that of the propelling member is connected to the rear end side in the insertion direction than the propelling member.

7. The medical instrument according to claim 6, further comprising:
   an air supply opening portion provided on the distal end side in the insertion direction than a first contact member located on the most distal end side in the insertion direction in the contact member; and
   an air supply pipeline communicating with the air supply opening portion, inserted into the insertion portion and connected to an air supply device on the rear end side of the insertion portion in the insertion direction.

8. The medical instrument according to claim 1, wherein a plurality of the contact member is provided, the medical instrument further comprising:
   an air supply opening portion provided at a more distal position in the insertion direction than a first contact member of the plurality of contact members, the first contact member being located at the most distal position with respect to the plurality of contact members in the insertion direction; and
   an air supply pipeline communicating with the air supply opening portion, inserted into the insertion portion and connected to an air supply device on the rear end side of the insertion portion in the insertion direction.

9. The medical instrument according to claim 1, wherein between the propelling member and the contact member, a base with a diameter smaller than that of the propelling member is provided, and the suction opening portion is provided at the base.

10. The medical instrument according to claim 1, wherein a sucking preventing member is further provided so as to cover the suction opening portion.

11. The medical instrument according to claim 1, wherein between the propelling member and the contact member, a base with a diameter smaller than that of the propelling member is provided, and at the base, a first suction opening portion in the suction opening portion is provided, and
    a second suction opening portion in the suction opening portion is further provided at the propelling member.

12. The medical instrument according to claim 1, wherein the suction opening portion is formed in an elongated shape along an outer circumferential direction of the insertion portion.

13. The medical instrument according to claim 1, wherein the contact member is a balloon capable of inflation/deflation in the radial direction of the insertion portion.

14. The medical instrument according to claim 1, wherein the propelling member includes:
    a rotatable cylindrical body, and
    a spiral shaped portion, provided on an outer surface of the rotatable cylindrical body, configured to rotate to push a part of the insertion portion where the contact member and the suction opening portion are provided to advance in the insertion direction, thereby making the part of the insertion portion where the contact member and the suction opening portion are provided advance along the insertion direction without being rotated.

15. The medical instrument according to claim 1, wherein a contact pressure detecting member for detecting a contact pressure between the propelling member and a body wall of the subject is provided at the propelling member; and
    on the basis of a detection of the contact pressure by the contact pressure detecting member, a suction pressure from the suction opening portion is adjusted.

* * * * *